United States Patent
Champion et al.

(10) Patent No.: US 10,415,021 B2
(45) Date of Patent: *Sep. 17, 2019

(54) MUTATED FUCOSIDASE

(71) Applicant: Glycom A/S, Hørsholm (DK)

(72) Inventors: Elise Champion, Toulouse (FR);
Andreas Vogel, Leipzig (DE);
Sebastian Bartsch, Leipzig (DE);
Gyula Dekany, Sinnamon Park (AU)

(73) Assignee: GLYCOM A/S, Hørsholm (DK)

( * ) Notice: Subject to any disclaimer, the term of this patent is extended or adjusted under 35 U.S.C. 154(b) by 85 days.

This patent is subject to a terminal disclaimer.

(21) Appl. No.: 15/521,580

(22) PCT Filed: Oct. 23, 2015

(86) PCT No.: PCT/IB2015/058197
§ 371 (c)(1),
(2) Date: Apr. 24, 2017

(87) PCT Pub. No.: WO2016/063261
PCT Pub. Date: Apr. 28, 2016

(65) Prior Publication Data
US 2017/0313996 A1  Nov. 2, 2017

(30) Foreign Application Priority Data
Oct. 24, 2014 (EP) .................... 14190374

(51) Int. Cl.
| | |
|---|---|
| C12N 9/26 | (2006.01) |
| C12N 15/00 | (2006.01) |
| C12P 19/18 | (2006.01) |
| C07H 21/04 | (2006.01) |
| C12P 21/06 | (2006.01) |
| C12P 21/04 | (2006.01) |
| C12N 9/10 | (2006.01) |
| C12N 9/24 | (2006.01) |
| C12P 19/04 | (2006.01) |

(52) U.S. Cl.
CPC ............ *C12N 9/1051* (2013.01); *C12N 9/24* (2013.01); *C12N 9/2402* (2013.01); *C12P 19/04* (2013.01); *C12P 19/18* (2013.01); *C12Y 204/01* (2013.01); *C12Y 204/01065* (2013.01)

(58) Field of Classification Search
None
See application file for complete search history.

(56) References Cited

U.S. PATENT DOCUMENTS 8,361,756 B2    1/2013 Mills et al.

FOREIGN PATENT DOCUMENTS

| EP | 2522232 A1 | 11/2012 |
|---|---|---|
| WO | 2008033520 A2 | 3/2008 |
| WO | 2012127410 A1 | 9/2012 |
| WO | 2013190530 A1 | 9/2012 |
| WO | 2012156897 A1 | 11/2012 |
| WO | 2012156898 A1 | 11/2012 |
| WO | 2013190531 A1 | 12/2013 |

OTHER PUBLICATIONS

WO_029678277.1. NCBI Database. 2014.*
Altschul, S. F. et al., "Gapped BLAST and PSI-BLAST: a new generation of protein database search programs," Nucleic Acids Research, 1997, vol. 25(17), pp. 3389-3402.
Ashida, H. et al., "Two distinct alpha-L-fucosidases from Bifidobacterium bifidum are essential for the utilization of fucosylated milk oligosaccharides and glycoconjugates," Glycobiology, 2009, vol. 19(9), pp. 1010-1017.
Marchler-Bauer, A. et al., "CDD: a Conserved Domain Database for protein classification," Nucleic Acids Research, 2005, vol. 33, pp. D192-D196. doi: 10.1093/nar/gki069.
Murata, T. et al., "Enzymatic synthesis of alpha-L-fucosyl-N-acetyllactosamines and 3'-O-alpha-L-fucosyllactose utilizing alpha-L-fucosidases," Carbohydrate Research, 1999, vol. 320, pp. 192-199.
Osanjo et al., "Directed Evolution of the alpha-L-Fucosidase from Thermotoga maritima into an alpha-L-Transfucosidase," Biochemistry, 2007, vol. 46, pp. 1022-1033.
Osanjo, G. O. et al., "Engineering the functional fitness of transglycosidases and glycosynthases by directed evolution," African Journal of Biotechnology, 2011, vol. 10(10), pp. 1727-1735.
Sakurama, H. et al., "1,3-1,4-alpha-L-Fucosynthase That Specifically Introduces Lewis a/x Antigens into Type-1/2 Chains," The Journal of Biological Chemistry, 2012, vol. 287(20), pp. 16709-16719.
Sela, D. A. et al., "The genome sequence of *Bifidobacterium longum* subsp. *infantis* reveals adaptations for milk utilization within the infant microbiome," PNAS, 2008, col. 105(48), pp. 18964-18969.
Sela, D. A. et al., "*Bifidobacterium longum* subsp. *infantis* ATCC 15697 alpha-Fucosidases Are Active on Fucosylated Human Milk Oligosaccharides," Applied and Environmental Microbiology, 2012, vol. 78(3), pp. 795-803.
Urashima, T. et al. (2011) "Milk Ologosaccharides," New York, New York: Nova Biomedical Books.

* cited by examiner

*Primary Examiner* — Yong D Pak
(74) *Attorney, Agent, or Firm* — Neal, Gerber & Eisenberg LLP

(57) ABSTRACT

Mutated fucosidases are provided demonstrating improved properties in terms of thermal stability and transfucosidase synthetic performance compared with a wild type transfucosidase isolated from *Bifidobacterium longum* subsp. *infantis*.

27 Claims, No Drawings
Specification includes a Sequence Listing.

MUTATED FUCOSIDASE

STATEMENT REGARDING JOINT RESEARCH AGREEMENT

Aspects of the present invention were made by or on behalf of the below listed parties to a joint research agreement. The joint research agreement was in effect on or before the date aspects of the present invention were made and aspects of the present invention were made as a result of the activities undertaken within the scope of the joint research agreement. The parties to the joint research agreement are Glycom A/S and c-LEcta GmbH.

FIELD OF THE INVENTION

This invention relates to an α1-3/4 transfucosidase having increased transfucosidase synthetic activity, decreased hydrolytic activity and/or increased thermostability.

BACKGROUND OF THE INVENTION

A wild-type α1-3/4 fucosidase has been isolated from *Bifidobacterium longum* subsp. *infantis* ATCC 15697 (SEQ ID No. 18 of U.S. Pat. No. 8,361,756, Sela et al. *Proc. Natl. Acad. Sci. USA* 105, 18964 (2008), Sela et al. *Appl. Environ. Microbiol.* 78, 795 (2012); for its crystal structure see Sakurama et al. *J. Biol. Chem.* 287, 16709 (2012)). This fucosidase is encoded by a DNA sequence of 1437 nucleotides as set forth in the '756 patent, encoding a sequence of 478 amino acids. According to the '756 patent, human milk oligosaccharides ("HMOs") can be synthesized by contacting an oligosaccharide containing precursor with this wild-type fucosidase and then isolating a modified oligosaccharide containing precursor. The protein according to SEQ ID No. 18 of U.S. Pat. No. 8,361,756 is referred to as SEQ ID No. 1 in the present application.

However, the wild-type α1-3/4 fucosidase has not been entirely suitable for making fucosylated oligosaccharides, particularly fucosylated HMOs. Mutants of the enzyme have therefore been sought preferably having increased transfucosidase synthetic activity and/or decreased hydrolytic activity and/or increased thermostability, especially increased transfucosidase synthetic activity, decreased hydrolytic activity and increased thermostability.

SUMMARY OF THE INVENTION

The present invention relates to a mutated α1-3/4 transfucosidase having
  an amino acid sequence that is substantially identical to, that is having at least 75% sequence identity to the sequence from amino acid positions 56 to 345 of SEQ ID No. 1, and
  a mutation at least at one or more of amino acid positions 134, 135, 170, 174, 216, 221, 236, 237, 244, 245 or 282, preferably at 134, 135, 174, 216, 221 or 282, said amino acid numbering being according to SEQ ID no. 1.

Preferably, the mutated α1-3/4 transfucosidase comprises one or more of the following mutations:
  at position 134 Pro (P) is substituted by Ala, Arg, Asn, Asp, Cys, Gln, Glu, Gly, Ile, Leu, Lys, Met, Phe, Ser, Thr, Trp, Tyr or Val, preferably Arg, Glu, Gly, Lys or Ser, particularly Arg; and/or
  at position 135 Trp (W) is substituted by Ala, Arg, Asn, Asp, Gln, Glu, Gly, His, Ile, Leu, Lys, Met, Phe, Pro, Ser, Thr, Tyr or Val, preferably Ala, Asp, Asn, Glu, Gln, His, Phe, Leu, Lys, Val or Tyr, particularly Phe or Tyr; and/or
  at position 170 Trp (W) is substituted by Ala, Gly, Ile, Leu, Met, Phe, Pro, Tyr or Val, preferably Phe, and/or
  at position 174 Ala (A) is substituted by Arg, Asn, Asp, Cys, Gln, Glu, Gly, Ile, His, Leu, Lys, Met, Phe, Pro, Ser, Thr, Trp, Tyr or Val, preferably Arg, Asn, Cys, Glu, Ile, His, Leu, Lys, Met, Phe, Trp, Tyr or Val, particularly Asn, His or Phe; and/or
  at position 216 Asn (N) is substituted by Asp or Glu; and/or
  at position 221 Val (V) is substituted by Ala, Gly, Ile, Leu or Pro, preferably Ala, and/or
  at position 236 Ala (A) is substituted by Asp, Glu or His; and/or
  at position 237 Glu (E) is substituted by Asn or His; and/or
  at position 244 Gln (Q) is substituted by Ala, Arg, Gly, His, Leu, Ile, Lys, Pro or Val, preferably Arg, Gly, His, Leu or Lys; and/or
  at position 245 Gln (Q) is substituted by Asp or Glu, preferably Glu; and/or
  at position 282 Val (V) is substituted by Arg, Asn, Asp, Cys, Gln, Glu, Gly, Lys, Met, Phe, Pro, Ser, or Trp, preferably Arg, Lys, Phe, Glu or Trp, particularly Arg, Trp or Phe.

It is also provided a mutated α1-3/4 transfucosidase having
  an amino acid sequence that is substantially identical to, that is, having at least 75% sequence identity to, SEQ ID No. 1, and
  a mutation at least at one or more of amino acid positions 165, 168, 232, 237, 258, 260, 274 or 413, preferably 168, 237 or 413.

According to another aspect, the invention relates to a process for making a mutated α1-3/4 transfucosidase mentioned above comprising the steps of:
  (a) providing a DNA sequence encoding the mutated α1-3/4 transfucosidase, then
  (b) expressing the mutated α1-3/4 transfucosidase in a host cell transformed with the DNA sequence obtained in step (a).

Also, a method for synthesizing a fucosylated carbohydrate is provided comprising the step of reacting a fucosyl donor and a carbohydrate acceptor in the presence of a mutant α1-3/4 transfucosidase mentioned above to transfer the fucosyl residue of the fucosyl donor to the carbohydrate acceptor.

In a further aspect of the invention, use of a mutated α1-3/4 transfucosidase mentioned for the preparation of a fucosylated carbohydrate, preferably a fucosylated human milk oligosaccharide having an α1-3 and/or a α1-4 fucosyl residue, is provided.

DETAILED DESCRIPTION OF THE INVENTION

The first aspect of the invention relates to a mutated α1-3/4 fucosidase comprising a polypeptide fragment having:
  substantial identity (i.e. at least 75 percent (%) sequence identity) to a polypeptide fragment from amino acid position 56 to 345 of SEQ ID No.1, and
  mutation(s) (that is, an amino acid replaced by another amino acid) at one or more amino acid positions 134, 135, 170, 174, 216, 221, 236, 237, 244, 245 or 282, said amino acid numbering being according to SEQ ID No. 1, wherein at least one of the mutations is selected from:
- at position 134 Pro (P) is substituted by Ala, Arg, Asn, Asp, Cys, Gln, Glu, Gly, Ile, Leu, Lys, Met, Phe, Ser, Thr, Trp, Tyr or Val, preferably Arg, Glu, Gly, Lys or Ser, particularly Arg; and/or
- at position 135 Trp (W) is substituted by Ala, Arg, Asn, Asp, Gln, Glu, Gly, His, Ile, Leu, Lys, Met, Phe, Pro, Ser, Thr, Tyr or Val, preferably Ala, Asp, Asn, Glu, Gln, His, Phe, Leu, Lys, Val or Tyr, particularly Phe or Tyr; and/or
- at position 170 Trp (W) is substituted by Ala, Gly, Ile, Leu, Met, Phe, Pro, Tyr or Val, preferably Phe, and/or
- at position 174 Ala (A) is substituted by Arg, Asn, Asp, Cys, Gln, Glu, Gly, Ile, His, Leu, Lys, Met, Phe, Pro, Ser, Thr, Trp, Tyr or Val, preferably Arg, Asn, Cys, Glu, Ile, His, Leu, Lys, Met, Phe, Trp, Tyr or Val, particularly Asn, His or Phe; and/or
- at position 216 Asn (N) is substituted by Asp or Glu; and/or
- at position 221 Val (V) is substituted by Ala, Gly, Ile, Leu or Pro, preferably Ala, and/or
- at position 236 Ala (A) is substituted by Asp, Glu or His; and/or
- at position 237 Glu (E) is substituted by Asn or His; and/or
- at position 244 Gln (Q) is substituted by Ala, Arg, Gly, His, Leu, Ile, Lys, Pro or Val, preferably Arg, Gly, His, Leu or Lys; and/or
- at position 245 Gln (Q) is substituted by Asp or Glu, preferably Glu; and/or
- at position 282 Val (V) is substituted by Arg, Asn, Asp, Cys, Gln, Glu, Gly, Lys, Met, Phe, Pro, Ser, or Trp, preferably Arg, Lys, Phe, Glu or Trp, particularly Arg, Trp or Phe.

Thereby, a mutated α1-3/4 fucosidase can be obtained providing, in comparison with the wild-type α1-3/4 fucosidase of SEQ ID No. 1:
- increased transfucosidase synthetic performance in a reaction between a fucosyl donor and an acceptor to produce a fucosylated product, and/or
- significantly reduced, preferably practically undetectable, hydrolysis of the fucosylated product of such a reaction.

The term "practically undetectable hydrolysis of the fucosylated product" preferably means that if hydrolysis of the fucosylated product by the mutated α1-3/4 fucosidase of the present invention occurs, the presence of the hydrolysis products in the sample is below the detection level. The skilled person is aware of the limit of detection of the different analytical methods. Typically, enzyme hydrolysis experiments are followed by HPLC. Under the conditions used (see e.g. Examples 1 and 2) the hydrolysis products at below a concentration of about 1% cannot be detected.

Accordingly, the present invention provides a mutated α1-3/4 fucosidase comprising a polypeptide fragment having a sequence identity of at least 75% to a polypeptide fragment from amino acid position 56 to 345 of SEQ ID No.1, and
a) a mutation at one or more amino acid positions 134, 135, 170, 174, 216, 221, 236, 237, 244, 245 or 282, wherein at least one of the mutations is selected from:
- at position 134 Pro (P) is substituted by Ala, Arg, Asn, Asp, Cys, Gln, Glu, Gly, Ile, Leu, Lys, Met, Phe, Ser, Thr, Trp, Tyr or Val, preferably Arg, Glu, Gly, Lys or Ser, particularly Arg; and/or
- at position 135 Trp (W) is substituted by Ala, Arg, Asn, Asp, Gln, Glu, Gly, His, Ile, Leu, Lys, Met, Phe, Pro, Ser, Thr, Tyr or Val, preferably Ala, Asp, Asn, Glu, Gln, His, Phe, Leu, Lys, Val or Tyr, particularly Phe or Tyr; and/or
- at position 170 Trp (W) is substituted by Ala, Gly, Ile, Leu, Met, Phe, Pro, Tyr or Val, preferably Phe, and/or
- at position 174 Ala (A) is substituted by Arg, Asn, Asp, Cys, Gln, Glu, Gly, Ile, His, Leu, Lys, Met, Phe, Pro, Ser, Thr, Trp, Tyr or Val, preferably Arg, Asn, Cys, Glu, Ile, His, Leu, Lys, Met, Phe, Trp, Tyr or Val, particularly Asn, His or Phe; and/or
- at position 216 Asn (N) is substituted by Asp or Glu; and/or
- at position 221 Val (V) is substituted by Ala, Gly, Ile, Leu or Pro, preferably Ala, and/or
- at position 236 Ala (A) is substituted by Asp, Glu or His; and/or
- at position 237 Glu (E) is substituted by Asn or His; and/or
- at position 244 Gln (Q) is substituted by Ala, Arg, Gly, His, Leu, Ile, Lys, Pro or Val, preferably Arg, Gly, His, Leu or Lys; and/or
- at position 245 Gln (Q) is substituted by Asp or Glu, preferably Glu; and/or
- at position 282 Val (V) is substituted by Arg, Asn, Asp, Cys, Gln, Glu, Gly, Lys, Met, Phe, Pro, Ser, or Trp, preferably Arg, Lys, Phe, Glu or Trp, particularly Arg, Trp or Phe, and/or
b) increased transfucosidase synthetic performance in a reaction between a fucosyl donor and an acceptor to produce a fucosylated product, and/or significantly reduced, preferably practically undetectable, hydrolytic activity towards the fucosylated product of such a reaction, comparing to the wild-type α1-3/4 fucosidase of SEQ ID No. 1.

Moreover, the present invention provides a mutated α1-3/4 fucosidase, comprising a polypeptide fragment having a sequence identity of at least 75% to a polypeptide fragment from amino acid position 56 to 345 of SEQ ID No.1, and
a) a mutation at one or more amino acid positions 134, 135, 170, 174, 216, 221, 236, 237, 244, 245 or 282, wherein at least one of the mutations is selected from:
- at position 134 Pro (P) is substituted by Ala, Arg, Asn, Asp, Cys, Gln, Glu, Gly, Ile, Leu, Lys, Met, Phe, Ser, Thr, Trp, Tyr or Val, preferably Arg, Glu, Gly, Lys or Ser, particularly Arg; and/or
- at position 135 Trp (W) is substituted by Ala, Arg, Asn, Asp, Gln, Glu, Gly, His, Ile, Leu, Lys, Met, Phe, Pro, Ser, Thr, Tyr or Val, preferably Ala, Asp, Asn, Glu, Gln, His, Phe, Leu, Lys, Val or Tyr, particularly Phe or Tyr; and/or
- at position 170 Trp (W) is substituted by Ala, Gly, Ile, Leu, Met, Phe, Pro, Tyr or Val, preferably Phe, and/or
- at position 174 Ala (A) is substituted by Arg, Asn, Asp, Cys, Gln, Glu, Gly, Ile, His, Leu, Lys, Met, Phe, Pro, Ser, Thr, Trp, Tyr or Val, preferably Arg, Asn, Cys, Glu, Ile, His, Leu, Lys, Met, Phe, Trp, Tyr or Val, particularly Asn, His or Phe; and/or
- at position 216 Asn (N) is substituted by Asp or Glu; and/or at position 221 Val (V) is substituted by Ala, Gly, Ile, Leu or Pro, preferably Ala, and/or at position 236 Ala (A) is substituted by Asp, Glu or His; and/or at position 237 Glu (E) is substituted by Asn or His; and/or at position 244 Gln (Q) is substituted by Ala, Arg, Gly, His, Leu, Ile, Lys, Pro or Val, preferably Arg, Gly, His, Leu or Lys; and/or at position 245 Gln (Q) is substituted by Asp or Glu, preferably Glu; and/or at position 282 Val (V) is substituted by Arg, Asn, Asp, Cys, Gln, Glu, Gly, Lys, Met, Phe, Pro, Ser, or Trp, preferably Arg, Lys, Phe, Glu or Trp, particularly Arg, Trp or Phe, and/or, b) a mutation at one or more amino acid positions 165, 168, 232, 237, 258, 260 or 274, and/or c) increased transfucosidase synthetic performance in a reaction between a fucosyl donor and an acceptor to produce a fucosylated product, and/or significantly reduced, preferably practically undetectable, hydrolytic activity towards the fucosylated product of such a reaction, and/or enhanced stability, preferably enhanced thermostability, comparing to the wild-type α1-3/4 fucosidase of SEQ ID No. 1.

The polypeptide fragment from amino acid position 56 to 345 of SEQ ID No.1 has been identified as the conserved domain (a sequence alignment representing a protein domain conserved during molecular evolution of the α-L-fucosidase superfamily) of the α1-3/4 fucosidase from *Bifidobacterium longum* subsp. *infantis* ATCC 15697 by the Conserved Domain Database of the National Center for Biotechnology Information (http://www.ncbi.nlm.nih.gov). α-Fucosidases containing the conserved domain of the α1-3/4 fucosidase from *Bifidobacterium longum* subsp. *infantis* ATCC 15697 with a sequence identity of at least 75% are listed in Table 1.

TABLE 1

| Description | Identity | Accession Number |
| --- | --- | --- |
| α-L-fucosidase [*Bifidobacterium longum* subsp. *infantis* EK3] | 100% | KEY30716.1 |
| α-L-fucosidase [*Bifidobacterium longum*] | 93% | WP_013140205.1 |
| putative α1-3/4 fucosidase [*Bifidobacterium kashiwanohense* JCM 15439] | 92% | KFI63931.1 |
| putative α1-3/4 fucosidase [*Bifidobacterium scardovii*] | 75% | KFI94501.1 |

In accordance with this invention, the terms "substantial identity" and "substantially identical" in the context of two or more nucleic acid or amino acid sequences preferably mean that the two or more sequences are the same or have at least about 75% of nucleotides or amino acid residues that are the same when compared and aligned for maximum correspondence over a comparison window or designated sequences of nucleic acids or amino acids (i.e. the sequences have at least about 75 percent (%) identity). Percent identity of nucleic acid or amino acid sequences can be measured using a BLAST 2.0 sequence comparison algorithms with default parameters, or by manual alignment and visual inspection (see e.g. http://www.ncbi.nlm.nih.gov/BLAST/). In accordance with this invention, the percent identity of substantially identical polypeptide fragment from amino acid position 56 to 345 of SEQ ID No.1, or substantially identical amino acid sequence of SEQ ID No. 1, or substantially identical nucleic acid sequences encoding the polypeptide fragment from amino acid position 56 to 345 of SEQ ID No.1 or substantially identical nucleic acid sequences encoding the whole amino acid sequence of SEQ ID No.1 is preferably at least 80%, more preferably at least 85%, yet more preferably at least 90%, still even more preferably at least 92%, especially at least 93%, more especially at least 94%, even more especially at least 95%, yet even more especially at least 96%, particularly at least 97%, more particularly at least 98%, and most particularly at least 99%. Suitably, the definition preferably excludes 100% sequence identity, such as imposing a maximum limit on the sequence identity of 99.9%, 99.8%, or 99.7%, or requiring that at least one amino acid difference occurs between the sequences being compared. This definition also applies to the complement of a test sequence and to sequences that have deletions and/or additions, as well as those that have substitutions. An example of an algorithm that is suitable for determining percent identity and sequence similarity is the BLAST 2.2.20+ algorithm, which is described in Altschul et al. *Nucl. Acids Res.* 25, 3389 (1997). BLAST 2.2.20+ is used to determine percent sequence identity for the nucleic acids and proteins of the invention. Software for performing BLAST analyses is publicly available through the National Center for Biotechnology Information (http://www.ncbi.nlm.nih.gov/).

Fucosidases transfer a fucosyl residue from a donor oligosaccharide to an acceptor. If the acceptor is another carbohydrate (mono- or oligosaccharide) then the fucosidase acts as transfucosidase (able to make a fucosylated carbohydrate product). On the other hand, the same fucosidase can transfer the same fucosyl residue, which was added to the carbohydrate acceptor previously, from the product to a water molecule, acting thus as a hydrolase. The two processes take place concurrently. The overall synthetic performance is the ratio of the transfucosidase and hydrolysis activities. If the overall synthetic performance is below 1, then the hydrolysis activity is dominant, and if the overall synthetic performance is more than 1, then the transfucosidase activity is dominant. The experimental overall synthetic performance of the wild-type α1-3/4 fucosidase from *Bifidobacterium longum* subsp. *infantis* ATCC 15697 is about 0.03 (as determined in the 3-FL+LNnT ⇌ LNFP-III+Lac reaction, see Example 1).

By comparison, the mutant fucosidases of this invention show a much higher overall synthetic performance, preferably higher than 1, which means a much higher transfucosidase activity relative to hydrolytic activity. In this regard, a relatively low transfucosidase synthetic activity of a mutant of this invention can be compensated for by a significant reduction in the hydrolytic activity of the mutant that results in an improved synthetic performance (that is, the transfucosidase-mediated hydrolysis of the fucosylated product is significantly less than its transfucosidase-mediated synthesis, so that the equilibrium of the competing reactions is shifted to the product formation). Similarly, a relatively high hydrolytic activity of a mutant can be overcome by a significant improvement in its transfucosidase synthetic activity. The mutated α1-3/4 fucosidases of this invention show a substantial improvement in their transfucosidase synthetic performance over the wild-type fucosidase of SEQ ID No.1, that is, at least a 50-fold, preferably at least a 100-fold, more preferably at least a 500-fold, even more preferably a 1000-fold, particularly a 2000-fold improvement over the wild-type fucosidase. As a consequence of this increased transfucosidase synthetic performance, the amount of the mutated α1-3/4 transfucosidase of the invention, used in the synthesis of a fucosylated product, can be significantly reduced and reaction times can be significantly shortened, which can lower the costs of synthesizing fucosylated oligosaccharide products, particularly fucosylated HMOs.

Suitably, the mutant fucosidases of the invention are non-natural fucosidases, that is, they are not made in nature or naturally-occurring, but are made as a result of chemical synthesis, genetic engineering or similar methods in the laboratory, resulting in synthetic mutant fucosidases.

According to a preferred embodiment of the first aspect of the invention, the mutated α1-3/4 transfucosidase comprises a polypeptide fragment that has at least 75% sequence identity to the segment from amino acid positions 56 to 345 of SEQ ID No.1, and an amino acid mutation at least at one or more of the following amino acid positions: 134, 135, 174, 216, 221 and 282.

More preferably, the α1-3/4 transfucosidase of this first aspect comprises a polypeptide domain that has a sequence identity of at least 75% to the segment from amino acid positions 56 to 345 of SEQ ID No.1, and an amino acid mutation at least at amino acid position 174, and at one or more of the following amino acid positions: 134, 135, 170, 216, 221, 236, 237, 241, 244, 245 and 282, preferably at one or more of the following amino acid positions: 134, 135, 216, 221 and 282.

Also more preferably, the α1-3/4 transfucosidase of this first aspect comprises a polypeptide domain that has a sequence identity of at least 75% to the segment from amino acid positions 56 to 345 of SEQ ID No.1, and an amino acid mutation at least at amino acid position 135, and at one or more of the following amino acid positions: 134, 170, 174, 216, 221, 236, 237, 241, 244, 245 and 282, preferably at one or more of the following amino acid positions: 134, 135, 216, 221 and 282.

Even more preferably, the α1-3/4 transfucosidase of this first aspect comprises a polypeptide domain that has a sequence identity of at least 75% to the segment from amino acid positions 56 to 345 of SEQ ID No.1, and an amino acid mutation at least at amino acid positions 135 and 174, and at one or more of the following amino acid positions: 134, 170, 216, 221, 236, 237, 241 and 282, preferably at one or more of the following amino acid positions: 134, 216, 221 and 282.

Optionally, the α1-3/4 transfucosidase of this first aspect comprises a polypeptide domain that has a sequence identity of at least 75% to the segment from amino acid positions 56 to 345 of SEQ ID No.1, and an amino acid mutation at least at amino acid positions 135 and/or 174, and at one or more of the following amino acid positions: 134, 170, 216, 221, 236, 237, 241 and 282, preferably at one or more of the following amino acid positions: 134, 216, 221 and 282, and there is a further mutation at one or more of the following amino acid positions: 165, 168, 232, 237, 258, 260 or 274.

The combination of mutations as disclosed above imparts not only a further improved transfucosidase synthetic performance to the mutated enzyme but an enhanced stability, particularly temperature stability.

Yet more preferably, the α1-3/4 transfucosidase of this first aspect comprises polypeptide domain that has a sequence identity of at least 75% to the segment from amino acid positions 56 to 345 of SEQ ID No.1 as described above, and the following amino acid mutations, in which:

at position 135, Trp (W) is substituted by Phe (F) or Tyr (Y), at position 174, Ala (A) is substituted by Asn (N), His (H) or Phe (F), and there is at least one further mutation at the amino acid position selected from 165, 168, 232, 237, 258, 260 and 274, preferably from 165, 168, 232, 258, 260 and 274.

Preferably, the α1-3/4 transfucosidase of this first aspect comprises the sequence of the entire polypeptide domain from amino acid position 56 to 345 of SEQ ID No. 1 having the following mutations:

at position 135, Trp (W) is substituted by Phe (F) or Tyr (Y), at position 174, Ala (A) is substituted by Asn (N), His (H) or Phe (F), and there is at least one further mutation at the amino acid position selected from 165, 168, 232, 237, 258, 260 and 274, preferably from 165, 168, 232, 258, 260 and 274.

Within the first aspect of the invention concerning the provision of mutated α1-3/4 fucosidases having increased transfucosidase synthetic performance in a reaction between a fucosyl donor and an acceptor to yield a fucosylated product, it is preferred that the mutated α1-3/4 transfucosidase comprises an amino acid sequence that has a sequence identity of at least 75% to SEQ ID No.1, and an amino acid mutation at least at one or more of the following amino acid positions: 134, 135, 170, 174, 216, 221, 236, 237, 244, 245 and 282, preferably at least at one or more of the following amino acid positions: 134, 135, 174, 216, 221 and 282.

Accordingly, the present invention provides a mutated α1-3/4 fucosidase comprising an amino acid sequence that has a sequence identity of at least 75% to SEQ ID No.1 and a) a mutation at one or more amino acid positions 134, 135, 170, 174, 216, 221, 236, 237, 244, 245 or 282, and/or b) increased transfucosidase synthetic performance in a reaction between a fucosyl donor and an acceptor to produce a fucosylated product, and/or significantly reduced, preferably practically undetectable, hydrolytic activity towards the fucosylated product of such a reaction, comparing to the wild-type α1-3/4 fucosidase of SEQ ID No. 1.

Moreover, a mutated α1-3/4 fucosidase is provided comprising an amino acid sequence that has a sequence identity of at least 75% to SEQ ID No.1 and a) a mutation at one or more amino acid positions 134, 135, 170, 174, 216, 221, 236, 237, 244, 245 or 282, and/or, preferably and b) a mutation at one or more amino acid positions 165, 168, 232, 237, 258, 260, 274 or 413, and/or c) increased transfucosidase synthetic performance in a reaction between a fucosyl donor and an acceptor to produce a fucosylated product, and/or significantly reduced, preferably practically undetectable, hydrolytic activity towards the fucosylated product of such a reaction, and/or enhanced stability, preferably enhanced thermostability, comparing to the wild-type α1-3/4 fucosidase of SEQ ID No. 1.

α-Fucosidases containing a substantially identical amino acid sequence of SEQ ID No.1, that is α-fucosidases having at least about 75 percent sequence identity to SEQ ID No. 1, are listed in Table 2.

TABLE 2

| Description | Identity | Accession Number |
|---|---|---|
| α-L-fucosidase [*Bifidobacterium longum* subsp. *infantis* EK3] | 99% | KEY30716.1 |
| α-L-fucosidase [*Bifidobacterium longum*] | 88% | WP_013140205.1 |
| putative α1-3/4 fucosidase [*Bifidobacterium kashiwanohense* JCM 15439] | 87% | KFI63931.1 |

More preferably, the α1-3/4 transfucosidase comprises an amino acid sequence that has a sequence identity of at least 75% with SEQ ID No.1, and an amino acid mutation at least at amino acid position 174, and at one or more of the following amino acid positions: 134, 135, 170, 216, 221, 236, 237, 241, 244, 245 and 282, preferably at one or more of the following amino acid positions: 134, 135, 216, 221 and 282.

Also more preferably, the α1-3/4 transfucosidase comprises an amino acid sequence that has a sequence identity of at least 75% to SEQ ID No.1, and an amino acid mutation at least at amino acid position 135, and at one or more of the following amino acid positions: 134, 170, 174, 216, 221, 236, 237, 241, 244, 245 and 282, preferably at one or more of the following amino acid positions: 134, 135, 216, 221 and 282.

Even more preferably, the α1-3/4 transfucosidase comprises an amino acid sequence that has a sequence identity of at least 75% to SEQ ID No.1, and an amino acid mutation at least: at amino acid positions 135 and 174, and at one or more of the following amino acid positions: 134, 170, 216, 221, 236, 237, 241 and 282, preferably at one or more of the following amino acid positions: 134, 216, 221 and 282.

Optionally, the α1-3/4 transfucosidase comprises an amino acid sequence that has a sequence identity of at least 75% to SEQ ID No.1, and an amino acid mutation at least: at amino acid positions 135 and/or 174, and at one or more of the following amino acid positions: 134, 170, 216, 221, 236, 237, 241 and 282, preferably at one or more of the following amino acid positions: 134, 216, 221 and 282, and there is a further mutation at one or more of the following amino acid positions: 165, 168, 232, 237, 258, 260, 274 and 413.

The combination of mutations as disclosed above imparts not only a further improved transfucosidase synthetic performance to the mutated enzyme but an enhanced stability, particularly temperature stability.

Preferably, the α1-3/4 transfucosidase comprises an amino acid sequence that has a sequence identity of at least 75% to SEQ ID No.1 as described above, and an amino acid mutation:
  at amino acid position 135 and/or 174, and
  at least at an amino acid position selected from 168, 237 and 413.

Preferably, the α1-3/4 transfucosidase comprises, more preferably consists of, the sequence of SEQ ID NO 1 having mutations:
  at amino acid position 135 and/or 174, and
  at least at an amino acid position selected from 168, 237 and 413.

In this aspect, at position 135 Trp (W) is preferably substituted by Ala, Asp, Asn, Glu, Gln, His, Phe, Leu, Lys, Val or Tyr, more preferably Phe or Tyr; at position 168 Ser (S) is preferably substituted by Glu (E); at position 174, Ala (A) is preferably substituted by Arg, Asn, Cys, Glu, Ile, His, Leu, Lys, Met, Phe, Trp, Tyr or Val, more preferably Asn, His or Phe; at position 237, Glu (E) is preferably substituted by His (H); and at position 413, Glu (E) is substituted by Arg (R).

In a more preferred embodiment, the α1-3/4 transfucosidase comprises an amino acid sequence that has a sequence identity of at least 75% to SEQ ID No.1 as described above, and an amino acid mutation:
  at amino acid position 174, and
  at amino acid position 168 or 413.

In a more preferred embodiment, the α1-3/4 transfucosidase comprises, more preferably consists of, the sequence of SEQ ID No.1 as described above having mutations:
  at amino acid position 174, and
  at amino acid position 168 or 413.

In a more preferred embodiment, the α1-3/4 transfucosidase comprises an amino acid sequence that has a sequence identity of at least 75% to SEQ ID No.1 as described above, and an amino acid mutation:
  at amino acid position 135, and
  at amino acid position 168 or 413.

In a more preferred embodiment, the α1-3/4 transfucosidase comprises, more preferably consists of, the sequence of SEQ ID No.1 having mutations:
  at amino acid position 135, and
  at amino acid position 168 or 413.

In a more preferred embodiment, the α1-3/4 transfucosidase comprises an amino acid sequence that has a sequence identity of at least 75% to SEQ ID No.1 as described above, and mutations to the amino acid sequence at three positions selected from 135, 168, 174 and 413.

In a more preferred embodiment, the α1-3/4 transfucosidase comprises, more preferably consists of, the sequence of SEQ ID No. 1 having mutations to the amino acid sequence at three positions selected from 135, 168, 174 and 413.

Even more preferably, the α1-3/4 transfucosidase comprises an amino acid sequence that has a sequence identity of at least 75% to SEQ ID No.1 as described above, and an amino acid mutations:
  at amino acid position 174,
  at an amino acid position 135 or 168, and
  at amino acid position 413.

Even more preferably, the α1-3/4 transfucosidase comprises, more preferably consists of, the sequence of SEQ ID No.1 as described above having mutations:
  at amino acid position 174,
  at an amino acid position 135 or 168, and
  at amino acid position 413.

Even more preferably, the α1-3/4 transfucosidase comprises an amino acid sequence that has a sequence identity of at least 75% to SEQ ID No.1 as described above, and an amino acid mutations:
  at amino acid position 174,
  at an amino acid position 135 or 168,
  at amino acid position 413, and
  at amino acid position selected from 165, 232, 258, 260 and 274.

Even more preferably, the α1-3/4 transfucosidase comprises, more preferably consists of, the sequence of SEQ ID No.1 as described above having mutations:
  at amino acid position 174,
  at an amino acid position 135 or 168,
  at amino acid position 413, and
  at amino acid position selected from 165, 232, 258, 260 and 274.

The above combination of mutations imparts not only a further improved transfucosidase synthetic performance to the mutated enzyme but a further enhanced stability, particularly temperature stability while maintaining further improved transfucosidase synthetic performance. The mutations at 135, 165, 174, 232, 258, 260 and 274 are preferably the following:

at position 135, as W135F or W135Y,
at position 165, as P165E,
at position 174, as A174F, A174H or A174N,
at position 232, as R232A,
at position 258, as Q258R,
at position 260, as D260P,
at position 274, as N274A.

Another embodiment of the first aspect of the invention relates to a mutated α1-3/4 fucosidase that comprises a polypeptide fragment that has a sequence identity of at least 75% to the segment from amino acid position 56 to 345 of SEQ ID No.1, and a mutation of at least at amino acid position 174 or 282, preferably at least at both amino acids, to provide significantly or completely suppressed hydrolytic activity. In this regard, at position 174, Ala (A) is preferably replaced by Phe (F), Asn (N) or His (H) and/or at position 282, Val (V) is preferably replaced by Arg (R), Glu (E), His (H) or Lys (K). The suppressed hydrolytic activity is beneficial because the mutated enzyme then does not significantly degrade the donor and/or the product by hydrolysis. As a result, the transfucosidase reaction is no longer kinetically controlled, and a much better synthesis/hydrolysis ratio (meaning a better synthetic performance) can be achieved. Mutation at one or both, preferably both, of the above amino acid positions can provide at least a 100-fold, preferably at least a 1000-fold, more preferably at least a 10000-fold reduced hydrolytic activity towards the fucosylated products.

Accordingly, a mutated α1-3/4 fucosidase is provided having a) a polypeptide fragment that has a sequence identity of at least 75% to the fragment from amino acid position 56 to 345 of SEQ ID No.1, and a mutation at least at amino acid position 174 or 282, preferably at least at both amino acids, and/or b) significantly or completely suppressed hydrolytic activity, when compared to the protein according to SEQ ID No. 1.

In addition, according to a certain embodiment, a mutated α1-3/4 fucosidase that has a sequence identity of at least 75% to the fragment from amino acid position 56 to 345 of SEQ ID No.1, and mutation of at least the amino acid position 174 or 282, preferably at least both amino acid positions, and
at least the amino acid position 165, 168, 232, 237, 258, 260 or 274.

The combination of mutations as disclosed above imparts not only a significantly reduced, preferably practically undetectable, hydrolysis of the fucosylated product but an enhanced stability, particularly temperature stability.

Therefore a mutated α1-3/4 fucosidase is also provided, having a) a polypeptide fragment that has a sequence identity of at least 75% to the fragment from amino acid position 56 to 345 of SEQ ID No.1, mutation of at least the amino acid at position 174 or 282, preferably at least both amino acid positions, and at least the amino acid position 165, 168, 232, 237, 258, 260 or 274, and/or b) significantly or completely suppressed hydrolytic activity, and/or c) enhanced stability, particularly temperature stability, when compared to the protein according to SEQ ID No. 1.

Preferably, the mutated α1-3/4 fucosidase comprises an amino acid sequence that has a sequence identity of at least 75% to SEQ ID No.1, mutation of at least the amino acid at position 174 or 282, preferably at least both amino acid positions, more preferably at position 174, Ala (A) is preferably replaced by Phe (F), Asn (N) or His (H) and/or at position 282, Val (V) is preferably replaced by Arg (R), Glu (E), His (H) or Lys (K).

The second aspect of the invention relates to a mutated α1-3/4 fucosidase comprising an amino acid sequence that has a sequence identity of at least 75% to SEQ ID No.1 and at least one mutation at amino acid position 165, 168, 232, 237, 258, 260, 274 or 413. The so-mutated α1-3/4 fucosidase shows enhanced stability in comparison to the protein of SEQ ID No.1, preferably enhanced thermostability, which allows the synthesis of a fucosylated product to be carried out effectively under more stringent conditions, particularly higher temperatures, which frequently leads to faster reaction times.

Concerning this second aspect, the mutated α1-3/4 transfucosidase preferably comprises the following mutations:

Pro (P) in position 165 is replaced by Glu (E),
Ser (S) in position 168 is replaced by Glu (E),
Arg (R) in position 232 is replaced by Ala (A),
Glu (E) in position 237 is replaced by His (H),
Gln (Q) in position 258 is replaced by Arg (R),
Asp (D) in position 260 is replaced by Pro (P),
Asn (N) in position 274 is replaced by Ala (A) and/or
Glu (E) in position 413 is replaced by Arg (R).

Accordingly, a mutated α1-3/4 fucosidase is provided having a) an amino acid sequence that has a sequence identity of at least 75% to SEQ ID No.1 and at least one mutation at amino acid position 165, 168, 232, 237, 258, 260, 274 or 413, and/or b) enhanced stability, preferably enhanced thermostability in comparison to the protein of SEQ ID No.1.

Preferably, the α1-3/4 transfucosidase of this second aspect comprises at least two amino acid mutations at positions selected from 165, 168, 232, 237, 258, 260, 274 or 413.

Preferably, the α1-3/4 transfucosidase of this second aspect comprises at least two amino acid mutations, one of which is at position 413, and the other is selected from the group consisting of position 165, 168, 232, 237, 258, 260 and 274.

More preferably, the α1-3/4 transfucosidase of this second aspect comprises at least two amino acid mutations at positions selected from 168, 237 and 413.

Even more preferably, the α1-3/4 transfucosidase of this second aspect comprises at least two amino acid mutations, one of which is at position 413, and the other is selected from 168 and 237.

According to the third aspect of the invention, a method is provided for making a mutated α1-3/4 transfucosidase of the first or second aspect of the invention, comprising the steps of:

(a) providing a DNA sequence encoding the mutated α1-3/4 transfucosidase, then
(b) expressing the mutated α1-3/4 transfucosidase in a host cell transformed with the DNA sequence obtained in step (a).

Step (a) can be carried out in a conventional manner by making a mutant DNA sequence encoding the mutated α1-3/4 transfucosidase of the invention, from a DNA sequence encoding a protein comprising a polypeptide fragment that has a sequence identity of at least 75% to the fragment of amino acid positions 56 to 345 of SEQ ID No. 1, or comprising the fragment of amino acid positions 56 to 345 of SEQ ID No. 1, or comprising a polypeptide that has a sequence identity of at least 75% to SEQ ID No. 1, or comprising, preferably consisting of, the entire SEQ ID No. 1. In step (b) the so-mutated DNA sequence is then introduced at the gene level by usual molecular-biological methods. The DNA sequence of the enzyme variants can be cloned in an expression vector which can be introduced in an appropriate host expression strain such as E. coli, containing DNA plasmids with the required information for regulation of expression of the enzyme variant. The sequence encoding the enzyme variant can be placed under the control of an inducible promoter. As a result, by adding an inducer, the expression of the enzyme variant can be controlled (generally, isopropyl-β-D-thiogalactopyranoside (IPTG) is used). The so-transformed host cells are then cultured in conventional nutrient media (e.g. Lennox broth, minimal medium M9) and induced with IPTG. After expression, the biomass can be harvested by centrifugation. The mutated enzyme can be isolated from the biomass after appropriate cell lysis and purification. In this process, conventional centrifugation, precipitation, ultrafiltration and/or chromatographic methods can be used.

According to the fourth aspect of the invention, a method is provided for synthesizing a fucosylated carbohydrate by reacting a fucosyl donor and a carbohydrate acceptor in the presence of a mutated α1-3/4 transfucosidase of the first or second aspect of the invention, whereby the fucosyl residue of the fucosyl donor is transferred to the carbohydrate acceptor.

In the following paragraphs, the expression "may carry" is equivalent with the expression "optionally carries", and the expression "can be substituted" is equivalent with the expression "is optionally substituted".

The carbohydrate acceptor used in the fourth aspect of the invention can be any mono- or oligosaccharide, preferably an oligosaccharide of 3-10 monosaccharide units that the mutated α1-3/4 fucosidase is able to accept. The oligosaccharide acceptor preferably contains a N-acetyl-glucosamine unit which forms a N-acetyl-lactosaminyl (Galpβ1-4GlcNAcp) or a lacto-N-biosyl (Galpβ1-3GlcNAcp) fragment with an adjacent galactose and/or it contains a glucose unit which is advantageously at the reducing end and preferably has a free 3-OH group. More preferably, the oligosaccharide acceptor having 3-10 units comprises a N-acetyl-lactosaminyl or lacto-N-biosyl moiety and is of formula 1, or is a lactose derivative of formula 2

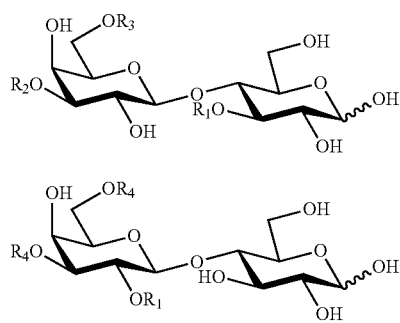

wherein $R_1$ is fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, and
each $R_4$ independently is sialyl or H,
with the proviso that at least one of $R_1$ or $R_4$ is not H.

Preferably, compounds of formula 1 are of formulae 1a or 1b

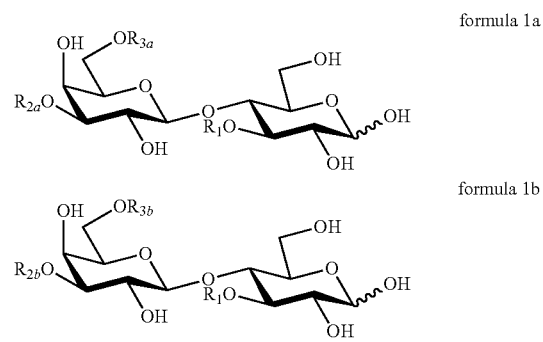

wherein $R_1$ is as defined above,
$R_{2a}$ is an N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue, but preferably void of a sialyl and/or fucosyl residue,
$R_{3a}$ is H or an N-acetyl-lactosaminyl group optionally substituted with a lacto-N-biosyl group; any N-acetyl-lactosaminyl and lacto-N-biosyl group can be substituted with one or more sialyl and/or fucosyl residue, but preferably void of a sialyl and/or fucosyl residue,
$R_{2b}$ is a lacto-N-biosyl group optionally substituted with sialyl and/or fucosyl residue, but preferably void of a sialyl and/or fucosyl residue, and
$R_{3b}$ is H or an N-acetyl-lactosaminyl group optionally substituted with one or two N-acetyl-lactosaminyl and/or one lacto-N-biosyl group; any N-acetyl-lactosaminyl and lacto-N-biosyl group can be substituted with one or more sialyl and/or fucosyl residue, but preferably void of a sialyl and/or fucosyl residue.

More preferably, compounds of formulae 1a and 1b have one or more of the following linkages and modifications:
the N-acetyl-lactosaminyl group in the glycosyl residue of $R_{2a}$ in formula 1a is attached to the another N-acetyl-lactosaminyl group by a 1-3 interglycosidic linkage,
the lacto-N-biosyl group in the glycosyl residue of $R_{2a}$ in formula 1a is attached to the N-acetyl-lactosaminyl group by a 1-3 interglycosidic linkage,
the lacto-N-biosyl group in the glycosyl residue of $R_{3a}$ in formula 1a is attached to the N-acetyl-lactosaminyl group by a 1-3 interglycosidic linkage, the N-acetyl-lactosaminyl group in the glycosyl residue of $R_{3b}$ in formula 1 b is attached to another N-acetyl-lactosaminyl group by a 1-3 or 1-6 interglycosidic linkage, and the lacto-N-biosyl group in the glycosyl residue of $R_{3b}$ in formula 1 b is attached to the N-acetyl-lactosaminyl group by a 1-3 interglycosidic linkage.

Even more preferably, a compound of formula 1a, 1b or 2 is selected from the group consisting of 2'-O-fucosyllactose (2'-FL), 3'-O-sialyllactose (3'-SL), lacto-N-tetraose (LNT), lacto-N-neotetraose (LNnT), lacto-N-fucopentaose I (LNFP-I, Fucα1-2Galβ1-3GlcNAcβ1-3Galβ1-4Glc), Galβ1-4GlcNAcβ1-3Galβ1-4[Fucα1-3]Glc, lacto-N-fucopentaose V (LNFP-V, Galβ1-3GlcNAcβ1-3Galβ1-4[Fucα1-3]Glc), Galβ1-4GlcNAcβ1-3Galβ1-4[Fucα1-3]Glc, lacto-N-hexaose (LNH, Galβ1-3GlcNAcβ1-3[Galβ1-4GlcNAcβ1-6]Galβ1-4Glc), lacto-N-neohexaose (LNnH, Galβ1-4GlcNAcβ1-3[Galβ1-4GlcNAcβ1-6]Galβ1-4Glc), para-lacto-N-hexaose (pLNH, Galβ1-3GlcNAcβ1-3Galβ1-4GlcNAcβ1-3Galβ1-4Glc), para-lacto-N-neohexaose (pLNnH, Galβ1-4GlcNAcβ1-3Galβ1-4GlcNAcβ1-3Galβ1-4Glc), fucosyl-LNH I (FLNH-I, Fucα1-2Galβ1-3GlcNAcβ1-3[Galβ1-4GlcNAcβ1-6]Galβ1-4Glc), fucosyl-LNH II (FLNH-II, Galβ1-4[Fucα1-3]GlcNAcβ1-6[Galβ1-3GlcNAcβ1-3]Galβ1-4Glc), fucosyl-para-LNH I (FpLNH-I, Galβ1-3GlcNAcβ1-3Galβ1-4[Fucα1-3]GlcNAcβ1-3Galβ1-4Glc), fucosyl-para-LNH II (FpLNH-II, Galβ1-3[Fucα1-4]GlcNAcβ1-3Galβ1-4GlcNAcβ1-3Galβ1-4Glc), Galβ1-4GlcNAcβ1-3Galβ1-4[Fucα1-3]GlcNAcβ1-3Galβ1-4Glc, Galβ1-4[Fucα1-3]GlcNAcβ1-3Galβ1-4GlcNAcβ1-3Galβ1-4Glc, difucosyl-LNH I (DFLNH-I, Galβ1-4[Fucα1-3]GlcNAcβ1-6[Fucα1-2Galβ1-3GlcNAcβ1-3]Galβ1-4Glc), difucosyl-para-LNH (DFpLNH, Galβ1-3[Fucα1-4]GlcNAcβ1-3Galβ1-4[Fucα1-3]GlcNAcβ1-3Galβ1-4Glc), difucosyl-para-LNnH (DFpLNnH, Galβ1-4[Fucα1-3]GlcNAcβ1-3Galβ1-4[Fucα1-3]GlcNAcβ1-3Galβ1-4Glc), lacto-N-octaose (LNO, Galβ1-3GlcNAcβ1-3[Galβ1-4GlcNAcβ1-3Galβ1-4GlcNAcβ1-6]Galβ1-4Glc), lacto-N-neooctaose (LNnO, Galβ1-4GlcNAcβ1-3[Galβ1-3GlcNAcβ1-3Galβ1-4GlcNAcβ1-6]Galβ1-4Glc), iso-lacto-N-octaose (iLNO, Galβ1-3GlcNAcβ1-3[Galβ1-3GlcNAcβ1-3Galβ1-4GlcNAcβ1-6]Galβ1-4Glc), para-lacto-N-octaose (pLNO, Galβ1-3GlcNAcβ1-3Galβ1-4GlcNAcβ1-3Galβ1-4GlcNAcβ1-3Galβ1-4Glc), LST a (NeuAcα2-3Galβ1-3GlcNAcβ1-3Galβ1-4Glc), LST c (NeuAcα2-6Galβ1-4GlcNAcβ1-3Galβ1-4Glc), sialyl-LNH (SLNH, Galβ1-3GlcNAcβ1-3[NeuAcα2-6Galβ1-4GlcNAcβ1-6]Galβ1-4Glc), sialyl-LNnH I (SLNnH-I, Galβ1-4GlcNAcβ1-3[NeuAcα2-6Galβ1-4GlcNAcβ1-6]Galβ1-4Glc), sialyl-LNnH II (SLNnH-II, Galβ1-4GlcNAcβ1-6[NeuAcα2-6Galβ1-4GlcNAcβ1-3]Galβ1-4Glc), disialyl-LNT (DSLNT, NeuAcα2-3Galβ1-3[NeuAcα2-6]GlcNAcβ1-3Galβ1-4Glc), fucosyl-sialyl-LNH (FSLNH, NeuAcα2-3Galβ1-3GlcNAcβ1-3[Galβ1-4[Fucα1-3]GlcNAcβ1-6]Galβ1-4Glc), fucosyl-sialyl-LNH II (FSLNH-II, Fucα1-2Galβ1-3GlcNAcβ1-3[NeuAcα2-6Galβ1-4GlcNAcβ1-6]Galβ1-4Glc), disialyl-LNH I (DSLNH-I, NeuAcα2-6Galβ1-4GlcNAcβ1-6[NeuAcα2-3Galβ1-3GlcNAcβ1-3]Galβ1-4Glc), disialyl-LNH II (DSLNH-II, Galβ1-4GlcNAcβ1-6[NeuAcα2-3Galβ1-3[NeuAcα2-6]GlcNAcβ1-3]Galβ1-4Glc) and disialyl-LNnH (DSLNnH, NeuAcα2-6Galβ1-4GlcNAcβ1-6[NeuAcα2-6Galβ1-4GlcNAcβ1-3]Galβ1-4Glc), advantageously 2'-FL, 3'-SL, LNT, LNnT, LNFP-I, LNFP-V, LNH, LNnH, pLNH, pLNnH and DSLNT.

A mutated α1-3/4 fucosidase of the first or second aspect of the invention demonstrates a strong α1-3/4 selectivity when carrying out the method of the fourth aspect of the invention. As a result, the product of the reaction is an α1-3- or a α1-4-fucosyl mono- or oligosaccharide, preferably an oligosaccharide of 3-10 monomer units, exclusively, and no an α1-2-fucosylated product can be detected. Preferably, the mutated α1-3/4 transfucosidase brings the fucosyl residue of an appropriate donor to the 3-position of the glucose in an acceptor of formula 2, to the 3-position of the N-acetyl-glucosamine in a, preferably terminal, N-acetyl-lactosaminyl group in an acceptor of formula 1, 1a or 1b, or to the 4-position of the N-acetyl-glucosamine in a, preferably terminal, lacto-N-biosyl group, in an acceptor of formula 1, 1a or 1 b. Accordingly, a mutated α1-3/4 transfucosidases of the invention is preferably used to synthesize fucosylated HMOs such as DFL, FSL, or those in which the fucosyl residue is attached to a GlcNAc moiety with α1-3 or α1-4 linkage, more preferably to the fucosylated HMOs listed in Table 3 below (for abbreviations see Urashima et al. *Milk Oligosaccharides*, Nova Science Publishers, NY, 2011, Table 4 in pp. 14-25).

TABLE 3

| acceptor | product |
|---|---|
| 2'-FL | DFL |
| 3'-SL | SFL |
| LNT | LNFP-II |
| LNnT | LNFP-III |
| LNFP-I | LNDFH-I |
| LNFP-V | LNDFH-II |
| Galβ1-4GlcNAcβ1-3Galβ1-4[Fucα1-3]Glc | LNDFH-III |
| LNH | FLNH-II |
| LNnH | Galβ1-4[Fucα1-3]GlcNAcβ1-3[Galβ1-4GlcNAcβ1-6]Galβ1-4Glc |
| LNnH | Galβ1-4GlcNAcβ1-3[Galβ1-4[Fucα1-3]GlcNAcβ1-6]Galβ1-4Glc |
| pLNH | FpLNH-I |
| pLNH | FpLNH-II |
| pLNH | DFpLNH |
| pLNnH | Galβ1-4GlcNAcβ1-3Galβ1-4[Fucα1-3]GlcNAcβ1-3Galβ1-4Glc |
| pLNnH | Galβ1-4[Fucα1-3]GlcNAcβ1-3Galβ1-4GlcNAcβ1-3Galβ1-4Glc |
| FpLNH-I | DFpLNH |
| FpLNH-II | DFpLNH |
| Galβ1-4GlcNAcβ1-3Galβ1-4[Fucα1-3]GlcNAcβ1-3Galβ1-4Glc | DFpLNnH |
| Galβ1-4[Fucα1-3]GlcNAcβ1-3Galβ1-4GlcNAcβ1-3Galβ1-4Glc | DFpLNnH |
| FLNH-I | DFLNH-I |
| FLNH-II | DFLNH-II |
| Galβ1-4[Fucα1-3]GlcNAcβ1-3[Galβ1-4GlcNAcβ1-6]Galβ1-4Glc | DFLNnH |
| Galβ1-4GlcNAcβ1-3[Galβ1-4[Fucα1-3]GlcNAcβ1-6]Galβ1-4Glc | DFLNnH |
| DFLNH-I | TFLNH |
| DFpLNnH | TFpLNnH |
| DFpLNH | TFpLNH-II |
| LST a | FLST a |
| LST c | FLST c |
| SLNH | FSLNH-III |
| SLNnH-II | FSLNnH-I |
| FSLNH | DFSLNH-I |
| FSLNH-II | DFSLNH-III |
| DSLNT | FDSLNT-I |
| DSLNH-II | FDSLNH-II |
| DSLNH-I | FDSLNH-III |
| DSLNnH | FDSLNnH |

The fucosyl donor used in the fourth aspect of the invention can be any fucosyl compound from which the mutated α1-3/4 fucosidase is able to transfer the fucosyl residue to a carbohydrate acceptor as described above. Accordingly, the fucosyl donor can be an α1-3 or α1-4 fucosyl saccharide, preferably of 3 or 4 monosaccharide units including the fucosyl residue, more preferably 3-FL or DFL, or a compound of formula 3

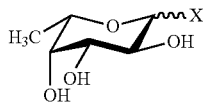

3 wherein X is selected from the group consisting of azide, fluoro, optionally substituted phenoxy, optionally substituted pyridinyloxy, group A, group B, group C and group D

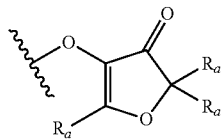

A

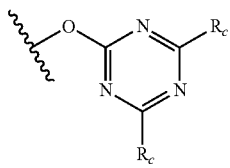

B

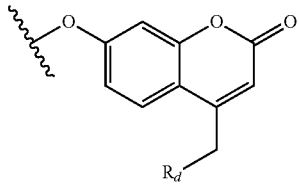

C

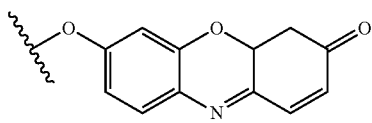

D wherein $R_a$ is independently H or alkyl, or two vicinal $R_a$ groups represent a =C($R_b$)$_2$ group, wherein $R_b$ is independently H or alkyl, $R_c$ is independently selected from the group consisting of alkoxy, amino, alkylamino and dialkylamino, $R_d$ is selected from the group consisting of H, alkyl and —C(=O)$R_e$, wherein $R_e$ is OH, alkoxy, amino, alkylamino, dialkylamino, hydrazino, alkylhydrazino, dialkylhydrazino or trialkylhydrazino, preferably X in formula 3 is selected from the group consisting of phenoxy-, p-nitrophenoxy-, 2,4-dinitrophenoxy-, 2-chloro-4-nitrophenoxy-, 4,6-dimethoxy-1,3,5-triazin-2-yloxy-, 4,6-diethoxy-1,3,5-triazin-2-yloxy-, 2-ethyl-5-methyl-3-oxo-(2H)-furan-4-yloxy-, 5-ethyl-2-methyl-3-oxo-(2H)-furan-4-yloxy- and 2,5-dimethyl-3-oxo-(2H)-furan-4-yloxy-group. Advantageously, the fucosyl donor is 3-FL or DFL.

A mutated α1-3/4 transfucosidase of the invention comprising a polypeptide that has a sequence identity of at least 75% to SEQ ID No.1, or comprising, preferably consisting of, the sequence of SEQ ID NO 1, and mutation at amino acid position 174 and at amino acid position 135 or 168, is especially suitable for making DFL, if the fucosyl donor is 3-FL and the carbohydrate acceptor is 2'-FL, LNFP-II, if the fucosyl donor is 3-FL or DFL and the acceptor is LNT, LNFP-III, if the fucosyl donor is 3-FL or DFL and the acceptor is LNnT, LNDFH-I, if the fucosyl donor is 3-FL or DFL and the acceptor is LNFP-I, and the product is Galβ1-4[Fucα1-3]GlcNAcβ1-3[Galβ1-4GlcNAcβ1-6]Galβ1-4Glc, Galβ1-4GlcNAcβ1-3[Galβ1-4[Fucα1-3]GlcNAcβ1-6]Galβ1-4Glc and/or DFLNnH, if the fucosyl donor is 3-FL or DFL and the acceptor is LNnH, Galβ1-4[Fucα1-3]GlcNAcβ1-3Galβ1-4GlcNAcβ1-3Galβ1-4Glc, if the fucosyl donor is 3-FL or DFL and the acceptor is pLNnH.

More preferably, in a fucosylation reaction, wherein the fucosyl donor is 3-FL and the acceptor is LNnT to make LNFP-III, LNT to make LNFP-II, LNFP-I to make LNDFH-I, pLNnH to make Galβ1-4[Fucα1-3]GlcNAcβ1-3Galβ1-4GlcNAcβ1-3Galβ1-4Glc, or 2'-FL to make DFL, the utilization of an α1-3/4 transfucosidase comprising an amino acid sequence having a sequence identity of at least 75% to SEQ ID No.1, and mutation of three amino acids position 174, at positions 135 or 168, and at position 413, and optionally having further mutation at amino acid position selected from 165, 232, 258, 260 and 274, or an α1-3/4 transfucosidase comprising, more preferably consisting of, the sequence of SEQ ID No. 1 having mutations of three amino acids at position 174, at positions 135 or 168, and at position 413, and optionally having further mutation at amino acid position selected from 165, 232, 258, 260 and 274, is especially favoured.

According to a fifth aspect of the invention, the use of a mutated α1-3/4 fucosidase of the first or second aspect of the invention is provided for synthesizing a fucosylated carbohydrate, preferably an α1-3 or a α1-4 fucosyl mono- or oligosaccharide, more preferably a fucosylated HMO having an α1-3 and/or a α1-4 fucosyl residue, even more preferably those in which the fucosyl residue is attached to a Glc moiety with α1-3 linkage or to a GlcNAc moiety with α1-3 or α1-4 linkage, especially one of the fucosylated HMOs listed in the Table 3 above, particularly DFL, SFL, LNFP-II, LNFP-III, LNDFH-I, fucosyl LNnH such as Galβ1-4[Fucα1-3]GlcNAcβ1-3[Galβ1-4GlcNAcβ1-6]Galβ1-4Glc or Galβ1-4GlcNAcβ1-3[Galβ1-4[Fucα1-3]GlcNAcβ1-6]Galβ1-4Glc, DFLNnH or fucosylated pLNnH such as Galβ1-4[Fucα1-3]GlcNAcβ1-3Galβ1-4GlcNAcβ1-3Galβ1-4Glc.

EXAMPLES

In the examples below mutants of *Bifidobacterium longum* subsp. *infantis* ATCC 15697 were tested, the position(s) of mutation is/are according to SEQ ID No. 1.

Example 1

Enhanced Transfucosidase Synthetic Performance of Mutants

The transfucosidase activity of mutants was investigated on the 3-FL+LNnT ⇌ LNFP-III+Lac reaction in which the formation of LNFP-III was followed.

The reaction was performed at 30° C. in 150 µl scale using 200 mM LNnT and 200 mM 3-FL. Samples were taken typically after 1 h, 2 h, 4 h and 20 h and the reaction was stopped by adding 390 µl of acetonitrile/water 1:1.

The hydrolytic activity of mutants was investigated in a similar procedure using LNFP-III (50 mM) as only substrate, and depletion of LNFP-III and formation of LNnT were followed over time.

HPLC conditions: Kinetex 2,6 µ HILIC 100A-column (150×4.6 mm) was used with a flow of 1.8 ml/min using 76% acetonitrile and 24% 10 mM ammonium formate buffer (pH 4). The elution of substrates and products was detected at 195 nm. For the quantification of LNnT and LNFP-III the peak areas were compared to an external standard.

The measured activity data are summarized in the table below. The synthetic performance was calculated as the ratio: synthesis [U/mg]/hydrolysis [U/mg], wherein 1U=production or hydrolysis of 1 µmol of LNFP-III per min.

| mutant | synthetic performance | improvement over WT |
|---|---|---|
| WT (wild type) | 0.031 | 1 |
| W135E | 3.3 | ≈100x |
| A174H | 27 | ≈850x |
| S168E-A174H-E413R | 110 | ≈3500x |
| W135E-A174F-V221A | 75 | ≈2400x |
| W135E-A174F | 225 | ≈7300x |
| W135E-A174F-E413R | 65 | ≈2100x |
| W135E-S168E-A174F | 45 | ≈1500x |
| W135E-A174F-E237H-E413R | 23 | ≈750x |
| W135E-S168E-A174F-E237H | 10 | ≈320x |
| W135E-A174F-E237H | 9 | ≈290x |
| W135F-A174N-E413R | 21 | ≈700x |
| W135F-A174N-N274A-E413R | 30 | ≈1000x |
| W135F-A174N-R232A-E413R | 23 | ≈750X |
| W135F-P165E-A174N-E413R | 28 | ≈900x |
| W135F-A174N-D260P-E413R | 23 | ≈750x |
| W135F-A174N-Q258R-E413R | 26 | ≈850x |

Example 2

Reduced Hydrolytic Activity of Mutants

The hydrolytic activity of mutants was investigated according to the procedure described in Example 1.

| mutant | hydrolysis [U/mg] |
|---|---|
| WT | 208 |
| W135E | 0.3 |
| A174H | 0.011 |
| S168E-A174H-E413R | 0.011 |
| W135E-A174F-V221A | 0.008 |
| W135E-A174F | 0.004 |
| W135E-A174F-E413R | 0.01 |
| W135E-S168E-A174F | 0.01 |
| W135E-A174F-E237H-E413R | 0.01 |
| W135E-S168E-A174F-E237H | 0.01 |
| W135E-A174F-E237H | 0.01 |
| W135F-A174N-E413R | 0.04 |
| W135F-A174N-N274A-E413R | 0.04 |
| W135F-A174N-R232A-E413R | 0.05 |
| W135F-P165E-A174N-E413R | 0.05 |
| W135F-A174N-D260P-E413R | 0.04 |
| W135F-A174N-Q258R-E413R | 0.05 |

Example 3

Enhanced Thermostability of Mutants

The melting temperature ($T_m$) is the temperature at which 50% of the initial activity of the enzyme remains after 15 min of incubation at elevated temperatures.

Activities were measured by HPLC analysis of 3-FL+LNnT ⇌ LNFP-III+Lac reaction in which the formation of LNFP-III was followed.

HPLC conditions: see above

Increasing the thermostability ($T_m$) of the wild type protein of SEQ ID No. 1:

| | 1 mutation | 2 mutations | 3 mutations |
|---|---|---|---|
| WT: 52° C. → | S168E: 58° C. → | S168E-E413R: 61° C. → | S168E-E237H-E413R: 63° C. |
| | E237H: 57° C. | E237H-E413R: 61° C. | |
| | E413R: 58° C. | | |

Increasing the thermostability of mutants designed for increased transfucosidase synthetic performance or reduced hydrolytic activity:

A174H: 58° C. → S168E-A174H-E413R: 62° C. → S168E-A174H-E237H-E413R: 66° C.

W135E-A174F: 51° C. → W135E-A174F-E413R: 54° C. → W135E-A174F-E237H-E413R: 58° C.
  W135E-S168E-A174F: 55° C.   W135E-S168E-A174F-E237H: 60° C.
  W135E-A174F-E237H: 56° C.

W135F-A174N-E413R: 58° C. → W135F-A174N-Q258R-E413R: 60° C.
  W135F-P165E-A174N-E413R: 61° C.
  W135F-A174N-D260P-E413R: 61° C.
  W135F-A174N-N274A-E413R: 62° C.
  W135F-A174N-R232A-E413R: 62° C.

Example 4

Transfucosidase Activity of Single-Point Mutants

A) Saturation mutagenesis was screened at positions 134, 135, 174 and 282 in the following reactions:

3-FL+LNnT 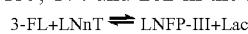 LNFP-III+Lac

3-FL+LNFP-I  LNDFH-I+Lac

The test was run in sodium phosphate buffer (50 mM, pH=6.5, 37° C., 150 µl), [3-FL]=200 mM, [LNnT]=200 mM, [LNFP-I]=200 mM, with 10 µl of crude enzyme extract. Conversions were measured after 15 min, 30 min, 60 min and 20 hours. The tables below show the conversions (%) after 30 min, 20 hours and the maximum conversion during the course. WT values are italic.

| | | conversion of LNFP-III (%) | | | | | | | | | | |
|---|---|---|---|---|---|---|---|---|---|---|---|---|
| | | P134 | | | W135 | | | A174 | | | V282 | | |
| | | 30 min | 20 h | max. conv. | 30 min | 20 h | max. conv. | 30 min | 20 h | max. conv. | 30 min | 20 h | max. conv. |
| A | Ala | 34 | 8 | 42 | 30 | 18 | 46 | 6 | 0 | 14 | 4 | 0 | 12 |
| R | Arg | 8 | 42 | 42 | 1 | 37 | 37 | 31 | 44 | 55 | 13 | 17 | 35 |
| N | Asn | 6 | 20 | 29 | 5 | 45 | 45 | 32 | 41 | 50 | 5 | 0 | 16 |
| D | Asp | 2 | 37 | 37 | 21 | 36 | 51 | 3 | 39 | 39 | 28 | 0 | 28 |
| C | Cys | 37 | 7 | 38 | 0 | 0 | 0 | 26 | 51 | 51 | 7 | 0 | 18 |
| Q | Gln | 1 | 27 | 27 | 2 | 27 | 27 | 2 | 23 | 23 | 0 | 0 | 0 |
| E | Glu | 24 | 0 | 24 | 17 | 35 | 51 | 19 | 54 | 54 | 23 | 0 | 23 |
| G | Gly | 23 | 24 | 45 | 0 | 25 | 25 | 30 | 8 | 30 | 4 | 0 | 15 |
| H | His | 0 | 0 | 0 | 7 | 44 | 44 | 30 | 59 | 61 | 5 | 0 | 13 |
| I | Ile | 9 | 18 | 30 | 9 | 40 | 40 | 6 | 51 | 51 | 4 | 0 | 11 |
| L | Leu | 25 | 0 | 26 | 4 | 47 | 47 | 25 | 46 | 60 | 4 | 0 | 8 |
| K | Lys | 4 | 39 | 39 | 4 | 46 | 46 | 32 | 49 | 55 | 16 | 15 | 32 |
| M | Met | 30 | 7 | 41 | 5 | 42 | 42 | 6 | 50 | 50 | 8 | 6 | 14 |
| F | Phe | 22 | 10 | 34 | 22 | 26 | 46 | 21 | 54 | 54 | 22 | 7 | 35 |
| P | Pro | *6* | *0* | *14* | 1 | 31 | 31 | 1 | 18 | 18 | 2 | 15 | 15 |
| S | Ser | 38 | 10 | 44 | 1 | 34 | 34 | 23 | 5 | 24 | 14 | 0 | 28 |
| T | Thr | 36 | 7 | 40 | 4 | 38 | 38 | 19 | 22 | 35 | 11 | 0 | 22 |
| W | Trp | 2 | 27 | 27 | *6* | *0* | *14* | 10 | 55 | 55 | 20 | 7 | 34 |
| Y | Tyr | 15 | 10 | 23 | 40 | 5 | 43 | 21 | 48 | 48 | 14 | 0 | 14 |
| V | Val | 35 | 7 | 35 | 14 | 27 | 44 | 24 | 22 | 43 | *6* | *0* | *14* |

| | | conversion of LNDFH-I (%) | | | | | | | | | | |
|---|---|---|---|---|---|---|---|---|---|---|---|---|
| | | P134 | | | W135 | | | A174 | | | V282 | | |
| | | 30 min | 20 h | max. conv. | 30 min | 20 h | max. conv. | 30 min | 20 h | max. conv. | 30 min | 20 h | max. conv. |
| A | Ala | 14 | 0 | 17 | 19 | 0 | 20 | *0* | *0* | *0* | 0 | 0 | 0 |
| R | Arg | 23 | 41 | 41 | 4 | 19 | 19 | 0 | 0 | 2 | 10 | 0 | 41 |
| N | Asn | 3 | 5 | 9 | 18 | 16 | 31 | 26 | 19 | 35 | 0 | 0 | 0 |
| D | Asp | 0 | 4 | 4 | 26 | 5 | 32 | 3 | 8 | 6 | 0 | 0 | 4 |
| C | Cys | 19 | 0 | 19 | 0 | 0 | 0 | 35 | 0 | 37 | 0 | 0 | 0 |
| Q | Gln | 11 | 9 | 16 | 9 | 38 | 38 | 0 | 0 | 0 | 0 | 0 | 0 |
| E | Glu | 35 | 5 | 38 | 20 | 4 | 26 | 12 | 9 | 12 | 0 | 0 | 0 |
| G | Gly | 22 | 0 | 22 | 2 | 27 | 27 | 10 | 0 | 13 | 0 | 0 | 0 |
| H | His | 0 | 0 | 0 | 3 | 31 | 31 | 8 | 21 | 21 | 0 | 0 | 0 |
| I | Ile | 7 | 0 | 9 | 14 | 21 | 25 | 0 | 5 | 5 | 0 | 0 | 0 |
| L | Leu | 10 | 0 | 10 | 2 | 27 | 27 | 4 | 19 | 19 | 0 | 0 | 0 |

-continued

| | conversion of LNDFH-I (%) | | | | | | | | | | | |
|---|---|---|---|---|---|---|---|---|---|---|---|---|
| | | P134 | | | W135 | | | A174 | | | V282 | |
| | | 30 min | 20 h | max. conv. | 30 min | 20 h | max. conv. | 30 min | 20 h | max. conv. | 30 min | 20 h | max. conv. |
| K | Lys | 36 | 31 | 40 | 3 | 22 | 22 | 0 | 4 | 4 | 0 | 0 | 12 |
| M | Met | 17 | 0 | 18 | 11 | 24 | 24 | 0 | 14 | 14 | 3 | 5 | 6 |
| F | Phe | 13 | 0 | 13 | 31 | 0 | 31 | 26 | 12 | 34 | 17 | 0 | 17 |
| P | Pro | 0 | 0 | 0 | 0 | 3 | 3 | 0 | 6 | 6 | 6 | 0 | 6 |
| S | Ser | 16 | 0 | 16 | 4 | 16 | 16 | 5 | 0 | 6 | 0 | 0 | 0 |
| T | Thr | 16 | 0 | 16 | 12 | 11 | 18 | 11 | 6 | 17 | 0 | 0 | 0 |
| W | Trp | 3 | 12 | 12 | 0 | 0 | 0 | 7 | 20 | 20 | 10 | 0 | 10 |
| Y | Tyr | 9 | 0 | 9 | 15 | 0 | 20 | 30 | 27 | 37 | 0 | 0 | 0 |
| V | Val | 6 | 0 | 8 | 14 | 5 | 18 | 22 | 0 | 22 | 0 | 0 | 0 |

B) In 3-FL+LNnT ⇌ LNFP-III+Lac reaction

The test was run in sodium phosphate buffer (50 mM, pH=6.5, 37° C., 200 µl), [3-FL]=200 mM, [LNnT]=200 mM, enzyme extract=2 or 0.5 mg/ml.

HPLC conditions: TSK Gel amide 80 (Tosoh, 3 µm, 150×4.6mm) was used with a flow of 1 ml/min using 56% acetonitrile and 44% water. The elution of substrates and products was detected by CAD and/or UV detection at 195 nm.

The tables show the LNFP-III formation (%) as a function of time.

| enzyme extract concentration: 2 mg/ml | | | | | | |
|---|---|---|---|---|---|---|
| | 15 min | 30 min | 1 hour | 2 hours | 4 hours | 6 hours | 22 hours |
| N216D | 29.73 | 23.27 | 4.83 | 2.51 | 0.44 | 0.33 | 0.00 |
| V221A | 24.19 | 16.40 | 1.00 | 0.00 | 0.00 | 0.00 | 0.00 |
| V282K | 27.29 | 31.51 | 38.10 | 28.07 | 30.81 | 25.63 | 10.92 |
| P134A | 40.46 | 37.37 | 32.85 | 27.17 | 19.58 | 14.86 | 6.16 |
| W135F | 42.53 | 43.66 | 44.57 | 42.06 | 37.76 | 31.71 | 19.52 |
| W135A | 45.58 | 44.14 | 40.11 | 35.03 | 27.97 | 23.01 | 14.20 |
| W135E | 27.22 | 38.91 | 44.19 | 43.59 | 39.49 | 35.53 | 26.51 |
| W170F | 40.06 | 32.92 | 29.91 | 24.04 | 14.04 | 8.79 | 2.11 |
| A174S | 38.40 | 34.58 | 30.90 | 26.98 | 20.28 | 16.55 | 9.51 |
| A174H | 48.05 | 49.32 | 49.16 | 49.30 | 48.60 | 48.10 | 46.17 |
| Q244K | 10.61 | 3.48 | 3.48 | 1.46 | 0.25 | 0.00 | 0.00 |

| enzyme extract concentration: 0.5 mg/ml | | | | | | |
|---|---|---|---|---|---|---|
| | 15 min | 30 min | 1 hour | 2 hours | 4 hours | 7 hours | 20 hours |
| N216D | 29.00 | 28.00 | 28.00 | 22.50 | 14.60 | 3.00 | 0.00 |
| V221A | 26.00 | 22.00 | 20.50 | 14.60 | 7.80 | 2.00 | 0.00 |
| V282K | 7.70 | 9.20 | 13.80 | 21.60 | 27.00 | 21.00 | 17.80 |
| P134A | 27.80 | 30.00 | 32.00 | 32.00 | 27.60 | 12.00 | 9.60 |
| W135F | 7.60 | 10.40 | 17.40 | 25.25 | 34.20 | 30.40 | 28.50 |
| W135A | 17.60 | 21.90 | 30.00 | 36.00 | 35.30 | 18.00 | 15.60 |
| W135E | 7.00 | 10.40 | 18.90 | 27.90 | 36.30 | 31.80 | 29.30 |
| W170F | 27.30 | 28.70 | 29.90 | 32.00 | 28.80 | 9.80 | 7.70 |
| A174S | 21.20 | 23.40 | 23.30 | 27.30 | 25.20 | 7.30 | 7.20 |
| A174H | 17.20 | 19.90 | 26.30 | 34.00 | 42.00 | 44.00 | 44.00 |
| Q244K | 22.50 | 21.25 | 15.90 | 12.10 | 6.50 | 0.00 | 0.00 |

C) In 3-FL+LNT ⇌ LNFP-II+Lac reaction

The test was run in sodium phosphate buffer (50 mM, pH=6.5, 37° C., 200 µl), [3-FL]=200 mM, [LNT]=200 mM, enzyme extract=0.5 mg/ml. HPLC: see Example 4 B). The table shows the LNFP-II formation (%) as a function of time.

| | 15 min | 30 min | 1 hour | 2 hours | 4 hours | 6.5 hours | 25 hours |
|---|---|---|---|---|---|---|---|
| N216D | 43.9 | 39.7 | 34.2 | 28.8 | 20.7 | 16.3 | 5.4 |
| V221A | 35.6 | 31.7 | 25.8 | 18.0 | 10.7 | 6.2 | 0.7 |
| V282K | 20.8 | 27.6 | 31.8 | 30.2 | 39.7 | 38.6 | 25.9 |
| P134A | 13.4 | 19.7 | 26.7 | 34.6 | 36.4 | 34.6 | 23.2 |
| W135F | 44.5 | 44.1 | 41.7 | 37.4 | 31.2 | 29.5 | 23.7 |
| W135A | 21.5 | 25.8 | 31.7 | 39.5 | 45.4 | 46.1 | 40.7 |
| W135E | 39.4 | 43.2 | 45.2 | 45.6 | 42.2 | 39.7 | 29.2 |
| W170F | 17.2 | 22.8 | 30.0 | 38.6 | 45.9 | 46.7 | 41.2 |
| A174S | 45.1 | 44.0 | 43.0 | 40.0 | 32.6 | 29.9 | 16.0 |
| A174H | 40.1 | 40.7 | 39.9 | 36.9 | 32.1 | 28.5 | 18.8 |
| Q244K | 37.6 | 41.2 | 45.1 | 48.8 | 50.5 | 50.5 | 50.2 |

D) In 3-FL+LNnH ⇌ Galβ1-4[Fucα1-3]GlcNAcβ1-3[Galβ1-4GlcNAcβ1-6]Galβ1-4Glc+Galβ1-4GlcNAcβ1-3[Galβ1-4[Fucα1-3]GlcNAcβ1-6]Galβ1-4Glc+DFLNnH+Lac reaction The test was run in sodium phosphate buffer (50 mM, pH=6.5, 37° C., 200 µl), [3-FL]=200 mM, [LNnH]=100 mM, enzyme extract=0.5 mg/ml. HPLC: see Example 4 B). The tables show the monofucosylated and difucosylated LNnH formation (%), respectively, as a function of time.

| | 15 min | 30 min | 1 hour | 2 hours | 4 hours | 6.5 hours | 25 hours |
|---|---|---|---|---|---|---|---|
| N216D | 0.0 | 4.8 | 11.8 | 10.8 | 0.0 | 0.0 | n.d. |
| V282K | 33.6 | 37.1 | 37.2 | 40.5 | 38.1 | 38.2 | 27.1 |
| P134A | 16.1 | 25.1 | 29.7 | 31.8 | 26.7 | 23.0 | 13.5 |
| W135F | 40.6 | 45.3 | 44.2 | 45.8 | 45.9 | 46.0 | 38.1 |
| W135A | 31.6 | 33.5 | 40.4 | 37.2 | 37.7 | 33.4 | 20.9 |
| W135E | 41.7 | 41.0 | 41.7 | 44.8 | 47.8 | 46.7 | 45.1 |
| W170F | 0.0 | 4.6 | 22.0 | 17.7 | 14.7 | 7.5 | 1.8 |
| A174S | 0.0 | 0.0 | 5.2 | 8.3 | n.d. | 6.0 | 3.8 |
| A174H | 49.6 | 49.8 | 49.4 | 48.4 | 49.6 | 49.2 | 49.7 |

| | 15 min | 30 min | 1 hour | 2 hours | 4 hours | 6.5 hours | 25 hours |
|---|---|---|---|---|---|---|---|
| N216D | 0.0 | 0.0 | 0.0 | 0.0 | 0.0 | 0.0 | n.d. |
| V282K | 3.2 | 5.7 | 6.4 | 7.2 | 6.3 | 5.1 | 2.3 |
| P134A | 0.0 | 2.0 | 3.0 | 4.0 | 3.5 | 1.8 | 0.0 |
| W135F | 9.1 | 13.7 | 12.5 | 14.7 | 16.3 | 13.8 | 6.3 |
| W135A | 3.4 | 4.1 | 8.9 | 7.3 | 6.3 | 4.5 | 0.3 |
| W135E | 10.2 | 9.1 | 8.4 | 11.2 | 16.1 | 16.3 | 11.4 |
| W170F | 0.0 | 0.0 | 0.0 | 0.0 | 0.0 | 0.0 | 0.0 |
| A174S | 0.0 | 0.0 | 0.0 | 0.0 | n.d. | 0.0 | 0.0 |
| A174H | 22.2 | 25.3 | 24.3 | 27.1 | 26.6 | 26.8 | 25.4 |

E) In 3-FL+pLNnH ⇌ Galβ1-4[Fucα1-3]GlcNAcβ1-3Galβ1-4GlcNAcβ1-3Galβ1-4Glc+Lac reaction The test was run in sodium phosphate buffer (50 mM, pH=6.5, 37° C., 200 µl), [3-FL]=100 or 200 mM, [pLNnH]=100 mM, enzyme extract=0.5 mg/ml. HPLC: see Example 4 B). The tables show the fucosylated pLNnH formation (%) as a function of time.

| | | | [3-FL] = 100 mM | | | | |
|---|---|---|---|---|---|---|---|
| | 15 min | 30 min | 1 hour | 2 hours | 4 hours | 6 hours | 25 hours |
| V282K | 3.5 | 4.8 | 5.3 | 5.6 | n.d. | 2.0 | 0.0 |
| P134A | 1.4 | 1.6 | 2.3 | 3.7 | 1.5 | 0.0 | 0.0 |
| W135F | 11.6 | 11.2 | 10.4 | 9.5 | 9.5 | 9.5 | 6.3 |
| W135A | 1.8 | 1.8 | 0.0 | 0.0 | 0.0 | 0.0 | 0.0 |
| W135E | 11.9 | 9.6 | 11.4 | 11.0 | 10.0 | 10.2 | 10.2 |
| W170F | 0.0 | 0.0 | 0.0 | 0.0 | 0.0 | 0.0 | 0.0 |
| A174S | 0.0 | 0.0 | 0.0 | 0.0 | 0.0 | 0.0 | 0.0 |
| A174H | 38.0 | 40.0 | 43.0 | 44.0 | 44.0 | 44.0 | 40.0 |
| Q244K | n.d. | n.d. | n.d. | n.d. | n.d. | n.d. | n.d. |

| | | | [3-FL] = 200 mM | | | | |
|---|---|---|---|---|---|---|---|
| | 15 min | 30 min | 1 hour | 2 hours | 4 hours | 6.5 hours | 25 hours |
| V282K | 27.0 | 35.5 | 31.0 | 34.7 | 30.8 | 29.5 | 7.8 |
| P134A | 10.6 | 20.8 | 28.5 | 25.7 | 19.6 | 14.0 | 6.4 |
| W135F | 43.8 | 47.7 | 49.0 | 48.0 | 43.9 | 39.1 | 21.2 |
| W135A | 21.8 | 28.9 | 36.1 | 32.6 | 25.8 | 19.0 | 10.2 |
| W135E | 46.0 | 42.3 | 45.6 | 46.0 | 35.2 | 41.5 | 25.2 |
| W170F | 0.0 | 4.3 | 7.3 | 3.1 | 2.7 | 1.0 | 0.0 |
| A174S | 0.0 | 3.0 | 2.7 | 4.3 | 1.8 | 1.2 | 0.0 |
| A174H | 57.6 | 60.1 | 59.8 | 60.7 | 60.7 | 60.6 | 58.1 |
| Q244K | 1.1 | 1.1 | 0.0 | 1.5 | 0.9 | 0.8 | 13.7 |

F) In 3-FL+LNFP-I ⇌ LNDFH-I+Lac reaction

The test was run in sodium phosphate buffer (50 mM, pH=6.5, 37° C., 200 µl), [3-FL]=200 mM, [LNFP-I]=200 mM, enzyme extract=0.5 mg/ml. HPLC: see Example 4 B). The table shows the LNDFH-I formation (%) as a function of time.

| | 15 min | 30 min | 1 hour | 2 hours | 4 hours | 6.5 hours | 25 hours |
|---|---|---|---|---|---|---|---|
| N216D | 43.3 | 40.9 | 28.3 | 35.7 | 30.6 | 26.8 | 18.2 |
| V221A | 35.5 | 35.2 | 20.9 | 28.5 | 23.5 | 16.5 | 7.6 |
| V282K | 11.0 | 14.6 | 17.4 | 24.3 | 30.7 | 34.1 | 36.8 |
| P134A | 38.7 | 41.7 | 43.7 | 45.3 | 44.8 | 43.3 | 39.2 |
| W135F | 18.9 | 22.0 | 24.9 | 32.4 | 41.1 | 45.6 | 51.9 |
| W135A | 23.1 | 29.7 | 33.0 | 37.3 | 42.7 | 44.3 | 43.3 |
| W135E | 9.5 | 13.1 | 16.9 | 25.2 | 35.8 | 39.6 | 50.7 |
| W170F | 47.3 | 42.4 | 44.5 | 42.0 | 38.0 | 35.6 | 29.0 |
| A174S | 21.8 | 24.5 | 25.6 | 28.7 | 29.9 | 30.7 | 31.7 |
| A174H | 0.9 | 2.0 | 2.7 | 2.9 | 29.4 | 6.5 | 15.7 |
| Q244K | 42.8 | 38.4 | 39.3 | 38.4 | 33.4 | 29.0 | 22.9 |

Another test was run in sodium phosphate buffer (50 mM, pH=6.5, 30° C., 140 µl), [3-FL]=50 mM, [LNFP-I]=50 mM, enzyme extract=10 µl. HPLC: see Example 1. The table shows the LNDFH-I formation (%) as a function of time.

| | 15 min | 4.5 h |
|---|---|---|
| WT | 10 | 0 |
| P134A | 33 | 17 |

| | 15 min | 4.5 h |
|---|---|---|
| P134V | 20 | 11 |
| W135F | 20 | 37 |
| W135A | 21 | 25 |
| W135E | 14 | 37 |
| W170F | 33 | 8 |
| A236D | 38 | 26 |
| A236H | 39 | 14 |
| E237N | 13 | 38 |
| Q244L | 42 | 14 |
| Q244H | 42 | 12 |
| Q244K | 36 | 11 |
| Q244G | 41 | 12 |
| Q244R | 31 | 8 |
| Q245E | 36 | 12 |

G) In DFL+LNnT ⇌ LNFP-III+2'-FL reaction

The test was run in sodium phosphate buffer (50 mM, pH=6.5, 37° C., 200 µl), [DFL]=200 mM, [LNnT]=200 mM, enzyme extract=0.5 mg/ml. HPLC: see Example 4 B). The table shows the LNFP-III formation (%) as a function of time.

| | 15 min | 30 min | 1 hour | 2 hours | 4 hours | 7 hours | 25 hours |
|---|---|---|---|---|---|---|---|
| N216D | 11.5 | 11.5 | 16.8 | 8.6 | 6.7 | 1.0 | 0.0 |
| V282K | 4.3 | 5.4 | 7.2 | 9.3 | 11.8 | 4.2 | 4.5 |
| P134A | 8.5 | 11.8 | 13.3 | 13.4 | 13.0 | 5.4 | 5.7 |
| W135F | 5.7 | 7.1 | 10.4 | 14.7 | 19.3 | 16.8 | 13.6 |
| W135A | 8.2 | 8.7 | 13.6 | 13.7 | 16.7 | 6.5 | 6.2 |
| W135E | 5.2 | 6.4 | 10.4 | 15.5 | 18.9 | 16.7 | 15.0 |
| W170F | 11.0 | 11.1 | 11.0 | 9.5 | 10.2 | 5.3 | 5.3 |
| A174S | 0.0 | 0.0 | 0.0 | 0.0 | 0.0 | 0.0 | 0.0 |
| A174H | 0.0 | 0.0 | 1.7 | 3.3 | 4.4 | 5.9 | 9.8 |
| Q244K | 5.9 | 5.5 | 4.5 | 4.3 | 3.5 | 2.2 | 1.0 |

H) In 3-FL+2'-FL ⇌ DFL+Lac reaction

The test was run in sodium phosphate buffer (50 mM, pH=6.5, 37° C., 200 µl), [3-FL]=200 mM, [2'-FL]=200 mM, enzyme extract=0.5 mg/ml. HPLC: see Example 4 B). The table shows the DFL formation (%) as a function of time.

| | 15 min | 30 min | 1 hour | 2 hours | 4 hours | 6 hours | 25 hours |
|---|---|---|---|---|---|---|---|
| N216D | 43.0 | 46.0 | 46.0 | 45.0 | 41.0 | 40.0 | 32.0 |
| V282K | 16.0 | 22.0 | 27.0 | 32.0 | 39.0 | 42.0 | 51.0 |
| P134A | 45.0 | 47.0 | 51.0 | 54.0 | 54.0 | 54.0 | 50.0 |
| W135F | 17.0 | 30.0 | 31.0 | 37.0 | 45.0 | 49.0 | 59.0 |
| W135A | 34.0 | 39.0 | 42.0 | 47.0 | 50.0 | 52.0 | 52.0 |
| W135E | 19.0 | 22.0 | 28.0 | 36.0 | 46.0 | 51.0 | 59.0 |
| W170F | 45.0 | 47.0 | 48.0 | 46.0 | 44.0 | 42.0 | 35.0 |
| A174S | 30.0 | 33.0 | 35.0 | 37.0 | 41.0 | 39.0 | 40.0 |
| A174H | 6.0 | 7.7 | 10.0 | 13.0 | 16.0 | 18.0 | 30.0 |
| Q244K | 31.0 | 33.0 | 33.0 | 32.0 | 31.0 | 30.0 | 19.0 |

Example 5

Multipoint Mutants

A) In 3-FL+LNnT ⇌ LNFP-III+Lac reaction

The test was run in sodium phosphate buffer (50 mM, pH=6.5, 37° C., 200 µl), [3-FL]=200 mM, [LNnT]=200 mM, enzyme extract=0.5 mg/ml. HPLC: see Example 4 B). The table shows the LNFP-III formation (%) as a function of time.

|  | 15 min | 30 min | 1 hour | 2 hours | 4 hours | 6 hours | 23 hours |
|---|---|---|---|---|---|---|---|
| S168E-A174H-E413R | 19.8 | 25.21 | 32.09 | 40.69 | 47.05 | 50.15 | 51.15 |
| S168E-A174F | 6.58 | 7.4 | 11.32 | 15.11 | 25.47 | 31.36 | 49.16 |
| S168E-A174H-V282E | 23.29 | 29.99 | 38.16 | 45.65 | 50.29 | 51.55 | 50.1 |
| S168E-A174H-V221A | 10.75 | 16.22 | 23.99 | 34.66 | 46.91 | 50.33 | 51.0 |
| S168E-A174H-V221A-V282H | 28.89 | 33.6 | 39.95 | 47.55 | 49.95 | 51.08 | 50.89 |
| W135E-A174F-V221A | 6.86 | 9.96 | 16.67 | 27.29 | 41.29 | 47.34 | 52.77 |
| S168E-A174F-V221A-V282R | 16.32 | 24.15 | 31.23 | 41.0 | 48.14 | 50.29 | 52.12 |
| S168E-A174H-N216D | 21.47 | 24.91 | 31.2 | 39.08 | 46.3 | 49.34 | 51.65 |
| W135E-A174F-N216D-V221A | 40.38 | 41.75 | 44.09 | 47.96 | 49.18 | 50.01 | 48.95 |
| S168E-A174H | 17.47 | 21.52 | 28.17 | 36.21 | 43.01 | 46.31 | 51.08 |

Another test was run in sodium phosphate buffer (50 mM, pH=6.5, 37° C., 150 µl), [3-FL]=200 mM, [LNT]=200 mM, enzyme extract=0.67 mg/ml. Samples were taken after 3, 10, 15, 20, 30, 45, 61 and 115 min. HPLC: see Example 1. The table shows the activity in [U/mg] wherein 1 U=production of 1 µmol LNFP-II per min.

|  | LNFP-III [U/mg] |
|---|---|
| W135F-A174N-E413R | 0.83 |
| W135F-A174N-N274A-E413R | 1.20 |
| W135F-A174N-R232A-E413R | 1.17 |
| W135F-P165E-A174N-E413R | 1.39 |
| W135F-A174N-Q258R-E413R | 1.32 |
| W135F-A174N-D260P-E413R | 0.90 |

B) In 3-FL+LNT ⇌ LNFP-II+Lac reaction

The test was run in sodium phosphate buffer (50 mM, pH=6.5, 37° C., 200 µl), [3-FL]=200 mM, [LNT]= 200 mM, enzyme extract=0.5 mg/ml. HPLC: see Example 4 B). The table shows the LNFP-II formation (%) as a function of time.

|  | 15 min | 30 min | 1 hour | 2 hours | 4 hours | 6 hours | 23 hours |
|---|---|---|---|---|---|---|---|
| S168E-A174H-E413R | 14.8 | 24.9 | 32.4 | 41.1 | 46.8 | 47.8 | 48.7 |
| S168E-A174F | 3.7 | 5.6 | 9.2 | 14.4 | 23.3 | 29.1 | 46.1 |
| S168E-A174H-V282E | 17.33 | 25.95 | 37.76 | 48.0 | 48.03 | 48.49 | 48.19 |
| S168E-A174H-V221A | 7.8 | 13.29 | 21.81 | 32.89 | 44.53 | 46.99 | 48.74 |
| S168E-A174H-V221A-V282H | 23.98 | 32.38 | 39.9 | 45.98 | 48.32 | 48.49 | 47.43 |
| W135E-A174F-V221A | 5.2 | 9.31 | 14.94 | 25.29 | 37.21 | 43.67 | 47.45 |
| S168E-A174F-V221A-V282R | 13.71 | 21.95 | 31.93 | 40.91 | 46.97 | 48.14 | 48.08 |
| S168E-A174H-N216D | 19.91 | 25.1 | 32.9 | 39.71 | 46.39 | 47.89 | 47.58 |
| W135E-A174F-N216D-V221A | 34.4 | 38.56 | 42.29 | 46.53 | 47.56 | 47.59 | 44.94 |
| S168E-A174H | 16.07 | 21.65 | 29.02 | 36.21 | 42.63 | 44.8 | 48.08 |

Another test was run in sodium phosphate buffer (50 mM, pH=6.5, 37° C., 150 µl), [3-FL]=200 mM, [LNT]=200 mM, enzyme extract=0.67 mg/ml. Samples were taken after 3, 10, 15, 20, 30, 45, 61 and 115 min. HPLC: see Example 1. The table shows the activity in [U/mg] wherein 1 U=production of 1µmol LNFP-II per min.

|  | LNFP-II [U/mg] |
|---|---|
| W135F-A174N-E413R | 0.92 |
| W135F-A174N-N274A-E413R | 1.16 |
| W135F-A174N-R232A-E413R | 1.39 |
| W135F-P165E-A174N-E413R | 1.28 |
| W135F-A174N-Q258R-E413R | 1.31 |
| W135F-A174N-D260P-E413R | 1.09 |

C) In 3-FL+pLNnH ⇌ Galβ1-4[Fucα1-3]GlcNAcβ1-3Galβ1-4GlcNAcβ1-3Galβ1-4Glc+Lac reaction The test was run in sodium phosphate buffer (50 mM, pH=6.5, 37° C., 200 µl), [3-FL]=100, [pLNnH]=100 mM, enzyme extract=0.5 mg/ml. HPLC: see Example 4 B). The table shows the fucosylated pLNnH formation (%) as a function of time.

|  | 15 min | 30 min | 1 hour | 2 hours | 4 hours | 6 hours | 23 hours |
|---|---|---|---|---|---|---|---|
| S168E-A174H-E413R | 26.1 | 32.25 | 40.54 | 45.64 | 49.44 | 50.79 | 50.0 |
| S168E-A174F | 9.08 | 9.17 | 15.73 | 24.1 | 35.3 | 41.27 | 48.94 |
| S168E-A174H-V282E | 21.4 | 31.55 | 39.69 | 46.61 | 50.64 | 50.6 | 49.09 |
| S168E-A174H-V221A | 13.14 | 21.01 | 30.18 | 42.49 | 49.8 | 50.74 | 50.13 |
| S168E-A174H-V221A-V282H | 34.96 | 38.79 | 46.77 | 49.0 | 51.02 | 50.24 | 48.07 |
| W135E-A174F-V221A | 9.71 | 14.7 | 22.21 | 33.64 | 45.31 | 50.31 | 52.07 |
| S168E-A174F-V221A-V282R | 19.62 | 28.51 | 38.66 | 46.41 | 49.41 | 50.42 | 51.53 |

-continued

|  | 15 min | 30 min | 1 hour | 2 hours | 4 hours | 6 hours | 23 hours |
|---|---|---|---|---|---|---|---|
| S168E-A174H-N216D | 29.14 | 34.9 | 40.1 | 46.49 | 50.9 | 50.66 | 49.0 |
| W135E-A174F-N216D-V221A | 42.31 | 45.09 | 46.34 | 46.87 | 46.67 | 47.23 | 42.6 |
| S168E-A174H | 26.69 | 32.46 | 41.38 | 45.87 | 48.6 | n.d. | n.d. |

D) In 3-FL+LNFP-I ⇌ LNDFH-I+Lac reaction

The test was run in sodium phosphate buffer (50 mM, pH=6.5, 37° C., 200 μl), [3-FL]=200 mM, [LNFP-1]=200 mM, enzyme extract=0.5 mg/ml. HPLC: see Example 4 B). The table shows the LNDFH-I formation (%) as a function of time.

|  | 15 min | 30 min | 1 hour | 2 hours | 4 hours | 6 hours | 23 hours |
|---|---|---|---|---|---|---|---|
| S168E-A174F | 3.17 | 3.65 | 5.22 | 6.91 | 10.78 | 12.72 | 25.72 |
| S168E-A174H-V221A | 2.68 | 2.99 | 5.12 | 6.42 | 10.67 | 12.52 | 24.75 |
| W135E-A174F-V221A | 3.52 | 6.76 | 8.44 | 12.52 | 19.4 | 22.98 | 41.21 |
| W135E-A174F-N216D-V221A | 10.89 | 11.97 | 12.95 | 16.97 | 21.65 | 25.23 | 38.46 |

Another test was run in sodium phosphate buffer (50 mM, pH=6.5, 37° C. 150 μl), [3-FL]=100 mM, [LNFP-1]=50 mM, enzyme extract=10 μl crude extract. HPLC: see example 1. The table shows the LNDFH-I formation (%) as a function of time.

|  | 7 min | 220 min |
|---|---|---|
| W135E-A174F-E413R | 6 | 40 |
| W135Y-A174V-E413R | 3 | 45 |
| W135F-A174F-E413R | 15 | 41 |
| W135Y-A174F-E413R | 28 | 52 |
| W135Y-A174G-E413R | 9 | 43 |
| W135F-A174N-E413R | 19 | 58 |
| W135Y-A174N-E413R | 20 | 57 |
| W135Q-A174N-E413R | 13 | 56 |
| W135Y-A174S-E413R | 14 | 47 |
| W135F-A174S-E413R | 11 | 52 |

Another test was run in sodium phosphate buffer (50 mM, pH=6.5, 30° C., 140 μl), [3-FL]=50 mM, [LNFP-1]=50 mM, enzyme extract=10 μl. HPLC: see Example 1. The table shows the LNDFH-I formation (%) as a function of time.

|  | 15 min | 4.5 h |
|---|---|---|
| W135E-A174F-A236E | 14 | 50 |
| W135E-A174F-L238A | 17 | 51 |
| W135E-A174F-T239H | 21 | 53 |
| W135E-A174F-E241H | 19 | 52 |

Another test was run in sodium phosphate buffer (50 mM, pH=6.5, 37° C., 150 μl), [3-FL]=200 mM, [LNFP-I]=200 mM, enzyme extract=0.67 mg/ml. Samples were taken after 3, 10, 15, 20, 30, 45, 61 and 115 min. HPLC: see Example 1. The table shows the activity in [U/mg] wherein 1U=production of 1 μmol LNDFH-I per min.

|  | LNDFH-I [U/mg] |
|---|---|
| W135E-A174F | 0.44 |
| W135E-A174F-E241A | 0.58 |

-continued

|  | LNDFH-I [U/mg] |
|---|---|
| W135E-A174F-A236H | 0.59 |
| W135F-A174N-E413R | 0.58 |
| W135F-A174N-N274A-E413R | 0.76 |
| W135F-A174N-R232A-E413R | 0.75 |
| W135F-P165E-A174N-E413R | 0.68 |
| W135F-A174N-Q258R-E413R | 0.45 |
| W135F-A174N-D260P-E413R | 0.64 |

E) In 3-FL+2'-FL ⇌ DFL+Lac reaction

The test was run in sodium phosphate buffer (50 mM, pH=6.5, 37° C., 150 μl), [3-FL]=200 mM, [2'-FL]=200 mM, enzyme extract=0.67 mg/ml. Samples were taken after 3, 10, 15, 20, 30, 45, 61 and 115 min. HPLC: see Example 1. The table shows the activity in [U/mg] wherein 1 U=production of 1 μmol 2'-FL per min.

|  | DFL [U/mg] |
|---|---|
| W135F-A174N-E413R | 0.39 |
| W135F-A174N-N274A-E413R | 0.84 |
| W135F-A174N-R232A-E413R | 0.69 |
| W135F-P165E-A174N-E413R | 0.85 |
| W135F-A174N-Q258R-E413R | 0.49 |
| W135F-A174N-D260P-E413R | 0.36 |

The invention claimed is:

1. A mutated α1-3/4 transfucosidase comprising
an amino acid sequence that has a sequence identity of at least 75% to the sequence from amino acid positions 56 to 345 of SEQ ID No.1; and
at least one mutation;
wherein the at least one mutation comprises a mutation:
at position 134, wherein Pro (P) is substituted by Ala, Arg, Asn, Asp, Cys, Gln, Glu, Gly, Ile, Leu, Lys, Met, Phe, Ser, Thr, Trp, Tyr, or Val;
at position 135, wherein Trp (W) is substituted by Ala, Arg, Asn, Asp, Gln, Glu, Gly, His, Ile, Leu, Lys, Met, Phe, Pro, Ser, Thr, Tyr, or Val;
at position 170, wherein Trp (W) is substituted by Ala, Gly, Ile, Leu, Met, Phe, Pro, Tyr, or Val;
at position 174, wherein Ala (A) is substituted by Arg, Asn, Asp, Cys, Gln, Glu, Gly, Ile, His, Leu, Lys, Met, Phe, Pro, Ser, Thr, Trp, Tyr, or Val;
at position 216, wherein Asn (N) is substituted by Asp or Glu;
at position 221, wherein Val (V) is substituted by Ala, Gly, Ile, Leu, or Pro;
at position 236, wherein Ala (A) is substituted by Asp, Glu, or His;
at position 237, wherein Glu (E) is substituted by Asn or His;
at position 244, wherein Gln (Q) is substituted by Ala, Arg, Gly, His, Leu, Ile, Lys, Pro, or Val;
at position 245, wherein Gln (Q) is substituted by Asp or Glu;
at position 282, wherein Val (V) is substituted by Arg, Asn, Asp, Cys, Gln, Glu, Gly, Lys, Met, Phe, Pro, Ser, or Trp;
or combinations thereof.

2. The mutated α1-3/4 transfucosidase according to claim 1, wherein the at least one mutation comprises a one or more mutations at amino acid positions: 134, 135, 174, 216, 221, or 282.

3. The mutated α1-3/4 transfucosidase according to claim 1, wherein the at least one mutation comprises
a mutation at amino acid position 174; and
at least one further mutation at one or more amino acid positions: 134, 135, 168, 170, 216, 221, 236, 237, 241, or 282.

4. The mutated α1-3/4 transfucosidase according to claim 3, wherein the at least one mutation comprises
mutations at amino acid positions 135 and 174; and
at least one further mutation at one or more amino acid positions: 134, 168, 170, 216, 221, 236, 237, 241, or 282.

5. The mutated α1-3/4 transfucosidase according to claim 1, wherein the at least one mutation comprises a mutation:
at position 135, wherein Trp (W) is substituted by Phe (F) or Tyr (Y);
at position 174, wherein Ala (A) is substituted by Asn (N), His (H) or Phe (F); and
at least one further mutation at one or more amino acid positions: 165, 168, 232, 237, 258, 260, or 274.

6. The mutated α1-3/4 transfucosidase according to claim 1, comprising
an amino acid sequence that has a sequence identity of at least 75% to SEQ ID No.1, and
at least one mutation at one or more amino acid positions: 134, 135, 170, 174, 216, 221, 236, 237, 244, 245, or 282 of SEQ ID No. 1.

7. The mutated α1-3/4 transfucosidase according to claim 6, wherein the at least one mutation comprises
a mutation at amino acid position 174; and
at least one further mutation at one or more of amino acid positions: 134, 135, 170, 216, 221, 236, 237, 241, or 282.

8. The mutated α1-3/4 transfucosidase according to claim 7, wherein the at least one mutation comprises
mutations at amino acid positions 135 and 174; and
at least one further mutation at one or more amino acid positions: 134, 170, 216, 221, 236, 237, or 282.

9. The mutated α1-3/4 transfucosidase according to claim 7, wherein the at least one mutation comprises
a mutation at amino acid positions 135 or 174, and
at least one further mutation at one or more amino acid positions: 168, 237, or 413.

10. The mutated α1-3/4 transfucosidase according to claim 9, wherein the at least one mutation, when present,
at position 135 the at least one mutation comprises Trp (W) substituted by Ala, Asp, Asn, Glu, Gln, His, Phe, Leu, Lys, Val, or Tyr;
at position 168 the at least one mutation comprises Ser (S) substituted by Glu (E);
at position 237 the at least one mutation comprises Glu (E) substituted by His (H);
at position 174 the at least one mutation comprises Ala (A) substituted by Arg, Asn, Cys, Glu, Ile, His, Leu, Lys, Met, Phe, Trp, Tyr, or Val; or at position 413 the at least one mutation comprises Glu (E) substituted by Arg (R).

11. The mutated α1-3/4 transfucosidase according to claim 9, wherein the at least one mutation comprises a first mutation at amino acid position 135 or 174 and a second mutation at amino acid position 168 or 413.

12. The mutated α1-3/4 transfucosidase according to claim 11, wherein the at least one mutation comprises three mutations at amino acid positions: 135, 168, 174, or 413.

13. The mutated α1-3/4 transfucosidase according to claim 12, wherein the at least one mutation comprises a fourth mutation at amino acid position: 165, 232, 258, 260, or 274.

14. The mutated α1-3/4 transfucosidase according to claim 1, wherein the at least one mutation comprises a mutation at amino acid position 174 or 282.

15. The mutated α1-3/4 transfucosidase according to claim 14, wherein the at least one mutation comprises a mutation
at position 174, wherein Ala (A) is substituted by Phe (F), Asn (N) or His (H);
at position 282, wherein Val (V) is substituted by Arg (R), Glu (E), His (H) or Lys (K); or
at position 174, wherein Ala (A) is substituted by Phe (F), Asn (N) or His (H) and at position 282, wherein Val (V) is substituted by Arg (R), Glu (E), His (H) or Lys (K).

16. A mutated α1-3/4 transfucosidase comprising
an amino acid sequence that has a sequence identity of at least 75% with SEQ ID No.1, and
at least one mutation at one or more of amino acid positions: 165, 168, 232, 237, 258, 260, 274, or 413.

17. The mutated α1-3/4 transfucosidase according to claim 16, wherein the at least one mutation comprises
a mutation at amino acid position 413; and
a further mutation at one or more amino acid positions: 165, 168, 232, 237, 258, 260, or 274.

18. The mutated α1-3/4 transfucosidase according to claim 16, wherein the at least one mutation comprises a mutation
at position 165, wherein Pro (P) is substituted by Glu (E);
at position 168, wherein Ser (S) is substituted by Glu (E);
at position 232, wherein Arg (R) is substituted by Ala (A);
at position 237, wherein Glu (E) is substituted by His (H);
at position 258, wherein Gln (Q) is substituted by Arg (R);
at position 260, wherein Asp (D) is substituted by Pro (P);
at position 274, wherein Asn (N) is substituted by Ala (A); or
at position 413, wherein Glu (E) is substituted by Arg (R).

19. The mutated α1-3/4 transfucosidase according to claim 1, comprising
an amino acid sequence with a percent identity of at least 80% to the sequence from amino acid positions 56 to 345 of SEQ ID No. 1, or
a percent identity of at least 80% to SEQ ID No. 1.

20. A process for making a mutated α1-3/4 transfucosidase of claim 1, comprising the steps of:
(a) providing a DNA sequence encoding the mutated α1-3/4 transfucosidase, then
(b) expressing the mutated α1-3/4 transfucosidase in a host cell transformed with the DNA sequence obtained in step (a).

21. A method for synthesizing a fucosylated carbohydrate comprising the step of reacting a fucosyl donor and a carbohydrate acceptor in the presence of a mutant α1-3/4 transfucosidase according to claim 1 to transfer the fucosyl residue of the fucosyl donor to the carbohydrate acceptor.

22. The method according to claim 21, wherein the fucosylated oligosaccharide is an α1-3 or an α1-4 fucosyl oligosaccharide.

23. The method according to claim 22, wherein the fucosylated oligosaccharide is a human milk oligosaccharide.

24. The method according to claim 21, wherein when the fucosyl donor is 3-fucosyllactose or difucosyllactose,
the acceptor is lacto-N-neotetraose to make lacto-N-fucopentaose III;
the acceptor is lacto-N-tetraose to make lacto-N-fucopentaose II;
the acceptor is lacto-N-fucopentaose I to make lacto-N-difucohexaose I; or
the acceptor is lacto-N-neohexaose to make Galβ1-4[Fucα1-3]GlcNAcβ1-3[Galβ1-4GlcNAcβ1-6]Galβ1-4Glc, Galβ1-4GlcNAcβ1-3[Galβ1-4[Fucα1-3]GlcNAcβ1-6]Galβ1-4Glc or difucosyllactose lacto-N-neohexaose;
the acceptor is para-lacto-N-neohexaose to make Galβ1-4[Fucα1-3]GlcNAcβ1-3Galβ1-4GlcNAcβ1-3Galβ1-4Glc; or
when the donor is 3-fucosyllactose, the acceptor is 2'-fucosyllactose to make difucosyllactose;
and wherein the mutated α1-3/4 transfucosidase is as defined in claim 11.

25. The method according to claim 24, wherein the fucosyl donor is 3-fucosyllactose and the acceptor is
lacto-N-neotetraose to make lacto-N-fucopentaose III;
lacto-N-tetraose to make lacto-N-fucopentaose II;
lacto-N-fucopentaose I to make lacto-N-difucohexaose I;
para-lacto-N-neohexaose to make Galβ1-4[Fucα1-3]GlcNAcβ1-3Galβ1-4GlcNAcβ1-3Galβ1-4Glc; or
2'-fucosyllactose to make difucosyllactose;
and wherein the mutant α1-3/4 transfucosidase is as defined in claim 12.

26. The mutated α1-3/4 transfucosidase according to claim 1, wherein the at least one mutation comprises a mutation:
at position 134, wherein Pro (P) is substituted by Arg;
at position 135, wherein Trp (W) is substituted by Phe or Tyr;
at position 170, wherein Trp (W) is substituted by Phe;
at position 174, wherein Ala (A) is substituted by Asn, His, or Phe;
at position 216, wherein Asn (N) is substituted by Asp or Glu;
at position 221, wherein Val (V) is substituted by Ala;
at position 236, wherein Ala (A) is substituted by Asp, Glu, or His;
at position 237, wherein Glu (E) is substituted by Asn or His;
at position 244, wherein Gln (Q) is substituted by Arg, Gly, His, Leu, or Lys;
at position 245, wherein Gln (Q) is substituted by Asp or Glu;
at position 282, wherein Val (V) is substituted by Arg, Trp, or Phe;
or combinations thereof.

27. The mutated α1-3/4 transfucosidase according to claim 9, wherein the at least one mutation consists of
a mutation at amino acid positions 135 and 174, and
at least one further mutation at one or more amino acid positions: 168, 237, or 413.

* * * * *

SEQUENCE LISTING

<160> NUMBER OF SEQ ID NOS: 1

<210> SEQ ID NO 1
<211> LENGTH: 478
<212> TYPE: PRT
<213> ORGANISM: Bifidobacterium longum subsp. infantis

<400> SEQUENCE: 1

```
Met Asn Asn Pro Ala Asp Ala Gly Ile Asn Leu Asn Tyr Leu Ala Asn
1               5                   10                  15

Val Arg Pro Ser Ser Arg Gln Leu Ala Trp Gln Arg Met Glu Met Tyr
            20                  25                  30

Ala Phe Leu His Phe Gly Met Asn Thr Met Thr Asp Arg Glu Trp Gly
        35                  40                  45

Leu Gly His Glu Asp Pro Ala Leu Phe Asn Pro Arg Asn Val Asp Val
    50                  55                  60

Asp Gln Trp Met Asp Ala Leu Val Ala Gly Gly Met Ala Gly Val Ile
65                  70                  75                  80

Leu Thr Cys Lys His His Asp Gly Phe Cys Leu Trp Pro Ser Arg Leu
                85                  90                  95

Thr Arg His Thr Val Ala Ser Ser Pro Trp Arg Glu Gly Lys Gly Asp
            100                 105                 110

Leu Val Arg Glu Val Ser Glu Ser Ala Arg Arg His Gly Leu Lys Phe
        115                 120                 125

Gly Val Tyr Leu Ser Pro Trp Asp Arg Thr Glu Glu Ser Tyr Gly Lys
    130                 135                 140

Gly Lys Ala Tyr Asp Asp Phe Tyr Val Gly Gln Leu Thr Glu Leu Leu
145                 150                 155                 160

Thr Gln Tyr Gly Pro Ile Phe Ser Val Trp Leu Asp Gly Ala Asn Gly
                165                 170                 175

Glu Gly Lys Asn Gly Lys Thr Gln Tyr Tyr Asp Trp Asp Arg Tyr Tyr
            180                 185                 190

Asn Val Ile Arg Ser Leu Gln Pro Asp Ala Val Ile Ser Val Cys Gly
        195                 200                 205

Pro Asp Val Arg Trp Ala Gly Asn Glu Ala Gly His Val Arg Asp Asn
    210                 215                 220

Glu Trp Ser Val Val Pro Arg Arg Leu Arg Ser Ala Glu Leu Thr Met
225                 230                 235                 240

Glu Lys Ser Gln Gln Glu Asp Asp Ala Ser Phe Ala Thr Thr Val Ser
                245                 250                 255

Ser Gln Asp Asp Asp Leu Gly Ser Arg Glu Ala Val Ala Gly Tyr Gly
            260                 265                 270

Asp Asn Val Cys Trp Tyr Pro Ala Glu Val Asp Thr Ser Ile Arg Pro
        275                 280                 285

Gly Trp Phe Tyr His Gln Ser Glu Asp Lys Val Met Ser Ala Asp
    290                 295                 300

Gln Leu Phe Asp Leu Trp Leu Ser Ala Val Gly Gly Asn Ser Ser Leu
305                 310                 315                 320

Leu Leu Asn Ile Pro Pro Ser Pro Glu Gly Leu Leu Ala Glu Pro Asp
                325                 330                 335

Val Gln Ser Leu Lys Gly Leu Gly Arg Arg Val Ser Glu Phe Arg Glu
            340                 345                 350

Ala Leu Ala Ser Val Arg Cys Glu Ala Arg Thr Ser Ser Ala Ser Ala
        355                 360                 365
```

-continued

```
Ala Ala Ala His Leu Val Asp Gly Asn Arg Asp Thr Phe Trp Arg Pro
    370             375             380

Asp Ala Asp Asp Ala Ala Pro Ala Ile Thr Leu Thr Leu Pro Gln Pro
385             390             395                 400

Thr Thr Ile Asn Ala Ile Val Ile Glu Glu Ala Ile Glu His Gly Gln
            405             410             415

Arg Ile Glu His Leu Arg Val Thr Gly Ala Leu Pro Asp Gly Thr Glu
            420             425             430

Arg Val Leu Gly Gln Ala Gly Thr Val Gly Tyr Arg Arg Ile Leu Arg
        435             440             445

Phe Asp Asp Val Glu Val Ser Ser Val Thr Leu His Val Asp Gly Ser
450             455             460

Arg Leu Ala Pro Met Ile Ser Arg Ala Ala Ala Val Arg Ile
465             470             475
```